United States Patent
Sodickson et al.

(10) Patent No.: US 7,511,492 B2
(45) Date of Patent: Mar. 31, 2009

(54) MAGNETIC RESONANCE IMAGING AND RADIO FREQUENCY IMPEDANCE MAPPING METHODS AND APPARATUS

(75) Inventors: Daniel K. Sodickson, Larchmont, NY (US); Aaron K. Grant, Allston, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 0 days.

(21) Appl. No.: 11/708,968

(22) Filed: Feb. 21, 2007

(65) Prior Publication Data
US 2007/0241753 A1    Oct. 18, 2007

Related U.S. Application Data

(60) Provisional application No. 60/775,171, filed on Feb. 21, 2006.

(51) Int. Cl.
*G01V 3/00* (2006.01)
(52) U.S. Cl. ...................................... 324/309
(58) Field of Classification Search ......... 324/300–322; 600/410–435
See application file for complete search history.

(56) References Cited

U.S. PATENT DOCUMENTS

| | | | |
|---|---|---|---|
| 6,194,898 B1 * | 2/2001 | Magnuson et al. | 324/300 |
| 6,397,095 B1 * | 5/2002 | Eyuboglu et al. | 600/411 |
| 6,865,494 B2 * | 3/2005 | Duensing et al. | 702/38 |
| 2004/0167421 A1 * | 8/2004 | Gregory et al. | 600/547 |
| 2005/0052182 A1 * | 3/2005 | Wollin | 324/307 |
| 2006/0125475 A1 * | 6/2006 | Sodickson et al. | 324/300 |
| 2007/0032739 A1 * | 2/2007 | Hashimshony et al. | 600/552 |
| 2007/0032747 A1 * | 2/2007 | Hashimshony et al. | 600/587 |

FOREIGN PATENT DOCUMENTS

| | | | |
|---|---|---|---|
| WO | WO 2004/026136 A1 | 4/2004 | |
| WO | WO 2005/001502 A1 | 1/2005 | |
| WO | WO 2007/017779 A2 | 2/2007 | |

OTHER PUBLICATIONS

Birgül, O. et al., "New Technique for High Resolution Absolute Conductivity Imaging Using Magnetic Resonance-Electrical Impedance Tomography (MR-EIT)," Proceedings of SPIE, Bellingham, VA, Feb. 18, 2001, pp. 880-888, vol. 4320.

(Continued)

*Primary Examiner*—Dixomara Vargas
(74) *Attorney, Agent, or Firm*—Wolf, Greenfield & Sacks, P.C.

(57) ABSTRACT

In one aspect, a method of obtaining magnetic resonance (MR) and radio-frequency impedance mapping (RFIM) data from a region of an object arranged proximate a plurality of radio-frequency (RF) coils is provided. The method comprises detecting nuclear magnetic resonance (NMR) signals emitted from the region to form, at least in part, first MR data, obtaining at least one impedance measurement from the plurality of RF coils to form, at least in part, first RFIM data, and computing a first RFIM map indicating a spatial distribution in the region of at least one dielectric property, the first RFIM map computed based, at least in part, on the first RFIM data and the first MR data.

25 Claims, 9 Drawing Sheets

OTHER PUBLICATIONS

Brandstätter, B. et al., "Multi Frequency Electrical Impedance Tomography," International Jornal for Computation and Mathematics in Electrical and Electronic Engineering, 2001, pp. 828-847, vol. 20, No. 3.

Glidewell M. E. et al., The Use of Magnetic Resonance Imaging Data and the Inclusion of Anisotropic Regions in Electrical Impedance Tomography, Biometical Sciences Instrumentation, 1993, pp. 251-257, vol. 29.

Korjenevsky A. et. al., "Magnetic Induction Tomography: Experimental Realization," Physiol. Meas., Institute of Physics Publishing, Bristol, Great Britain, Feb. 1, 2000, pp. 89-94, vol. 21, No. 1.

Wuebbeler G. et al., "Assessment of SAR Values and Coil Performance for an Adaptive 4-Channel 3T Proton Head Coil Array," 2004, Proc. Intl. Soc. Mag. Reson. Med., p. 665, vol. 11.

* cited by examiner

MAGNETIC RESONANCE IMAGING AND RADIO FREQUENCY IMPEDANCE MAPPING METHODS AND APPARATUS

RELATED APPLICATION

This application claims priority under 35 U.S.C. § 119(e) to U.S. Provisional Application Ser. No. 60/775,171, entitled "MAGNETIC RESONANCE IMAGING AND RADIO FREQUENCY IMPEDANCE MAPPING METHODS AND APPARATUS," filed on Feb. 21, 2006, which is herein incorporated by reference in its entirety.

FIELD OF INVENTION

The present invention relates to imaging techniques, and more particularly, to magnetic resonance imaging (MRI) and radio frequency impedance mapping (RFIM).

BACKGROUND

Various imaging techniques have been developed to image internal characteristics of an object of interest based on detecting one or more properties of the object. Applications include, but are not limited to, medical imaging to facilitate detection, diagnosis and/or treatment of biological anomalies within a subject patient, and security applications such as, detection of contraband, explosives or other prohibited subject matter in postal packages, passenger baggage, etc. Exemplary imaging techniques include x-ray computed tomography (CT), magnetic resonance imaging, electrical impedance tomography, ultrasonography, etc.

Magnetic resonance imaging (MRI) includes techniques for capturing images of the internal structure of an object of interest, for example, by non-invasively obtaining images of internal structure of the human body, and has been widely used as a diagnostic tool in the medical community. MRI exploits the nuclear magnetic resonance (NMR) phenomenon to distinguish different structures within an object of interest. For example, in biological subjects, MRI may be employed to distinguish between various tissues, organs, anatomical anomalies (e.g., tumors), and/or to image blood flow, blood perfusion, etc.

In general, MRI operates by manipulating spin characteristics of subject material. MRI techniques include aligning the spin characteristics of nuclei of the material being imaged using a generally homogeneous magnetic field and perturbing the magnetic field with periodic radio frequency (RF) pulses. To invoke the NMR phenomenon, one or more resonant coils may be provided proximate an object positioned within the magnetic field. The RF coils are adapted to generate RF pulses at a resonant frequency that matches a Larmor frequency of certain material within the object to excite the nuclei and cause the spin to briefly precess about an axis in the direction of the applied RF pulse, rather than in the direction of the applied magnetic field. The Larmor frequency is related to the rate at which a nuclear spin precesses about an axis, which is, in turn, proportional to the strength of the applied magnetic field. When the RF pulse subsides, the spins precess about and gradually realigns with the magnetic field, releasing energy that can be measured and used to form one or more images of the internal structure of the object being imaged.

The development of MRI imaging devices, referred to herein as MR scanners, has tended toward implementations that use higher magnetic field strengths. One benefit of higher magnetic field strengths includes a proportional increase in the signal-to-noise ratio (SNR) of the NMR signal emitted from a target region. In particular, the ratio of NMR signal strength to noise increases in an approximately linear fashion with increased magnetic field strength. This increase in SNR allows higher resolution images to be obtained using higher magnetic field strengths. The clinical standard for MRI scanners is poised to shift from 1.5 Tesla to 3 Tesla (T). MRI scanners capable of imaging a human body using a magnetic field of 7 T or higher are currently being tested at various research centers. In general, high field MRI refers to MR scanners operating at 3 T and above.

Spatial encoding of NMR signals emitted from a subject has traditionally been achieved by applying magnetic field gradients to localize the NMR effect. However, recent trends in MRI involve achieving at least some of the spatial encoding conventionally accomplished with magnetic field gradients by providing multiple and parallel RF transmit and/or receive coils. The MR technique of using multiple transmit and/or receive coils to image a subject is referred to herein as parallel MR. Parallel MR takes advantage of the spatial information available using an appropriately arranged array of RF coils, as discussed in further detail below.

In parallel MR, some number of the RF coils in an array may be independently excited (e.g., RF power may be transmitted over independent channels to multiple respective RF coils) and/or independently measured (e.g., measurements may be obtained/received from multiple RF coils over respective independent channels). Parallel MR has circumvented previous limits on speed and efficiency, effecting a reduction in image acquisition times and improving the spatial resolution of acquired images for any give acquisition time. As a result, parallel MR is becoming a generally important part of many modern MRI scanners. Manufacturers of MRI equipment are engaged in designing and producing ever larger numbers of independent channels for data transmission and reception.

Another method of obtaining properties from an object of interest includes examining changes in the resonant properties of RF coils in the presence of the object. When a resonant coil is placed in proximity of a load, for example, a patient or other object to be imaged, various properties of the resonant coil are affected. In MRI, this loading effect tends to negatively impact the operation of the device by shifting the resonant frequency of the coil and/or causing other generally undesirable changes in coil properties that may lead to reduced sensitivity and decreased efficacy in the coil's ability to appropriately induce the NMR effect. This loading effect depends in part on dielectric properties (e.g., conductivity, electrical permittivity, magnetic permeability, etc.) of the load and therefore varies with the loading object.

The effects of coil loading complicate MRI, since uncompensated shifts in the resonant properties of transmit and/or receive coils can significantly degrade image quality. In fact, resonant coils are often tuned or adjusted to compensate for the generally undesirable loading effect caused by the object being imaged, and coil designers must often sacrifice optimal detector performance in favor of overall robustness for a variety of loading conditions. However, the sensitivity of resonant coils to loading effects may be viewed as a detection mechanism, rather than an inconvenience, to effectively measure dielectric properties (e.g., conductivity, permittivity, permeability, etc.) of an object proximate to the coil(s). In particular, a change in resonant properties of one or more resonant coils due to loading may provide information about the distribution of dielectric characteristics of the loading object.

The imaging modality using changes in coil resonance to characterize one or more dielectric properties of a loading object is referred to herein as radio frequency impedance mapping (RFIM), and describes generally any of various methods of mapping resonant properties and/or impedance characteristics of one or more resonant coils to dielectric properties of a body coupled to the one or more resonant coils. Details of this imaging modality and are described in Patent Cooperation Treaty (PCT) Publication WO2004/026136 ('136), entitled "Radio Frequency Impedance Mapping," and U.S. application Ser. No. 10/527,592 ('592), entitled "Radio Frequency Impedance Mapping."

In brief, one RFIM approach involves transmitting an RF signal along each of a plurality of coils in a resonant RF coil array and measuring the received responses in all of the other coils in the array. Such measurements may be performed first in the absence, and then in the presence, of an object to be imaged. The measurements may then be compared with a computational model of the coil array and the imaged object. Values may be chosen for one or more of conductivity, permittivity, and permeability of each region of the object. The model may then be adjusted until it best matches the experimental data obtained from the RF coil measurements. The result is a map (e.g., an image) of the spatial distribution of dielectric properties throughout the object.

SUMMARY OF THE INVENTION

Some embodiments according to the present invention include a method of obtaining magnetic resonance (MR) and radio-frequency impedance mapping (RFIM) data from a region of an object arranged proximate a plurality of radio-frequency (RF) coils, the method comprising detecting nuclear magnetic resonance (NMR) signals emitted from the region to form, at least in part, first MR data, obtaining at least one impedance measurement from the plurality of RF coils to form, at least in part, first RFIM data, and computing a first RFIM map indicating a spatial distribution in the region of at least one dielectric property, the first RFIM map computed based, at least in part, on the first RFIM data and the first MR data.

Some embodiments of the present invention include a method of obtaining magnetic resonance (MR) and radio-frequency impedance mapping (RFIM) data from a region of an object arranged proximate a plurality of radio-frequency (RF) coils, the methods comprising obtaining at least one impedance measurement from the plurality of coils to form, at least in part, first RFIM data, computing a first RFIM map indicating a spatial distribution in the region of at least one dielectric property of the object based, at least in part, on the first RFIM data, forming at least one specific absorption ratio (SAR) map indicating a spatial distribution of SAR values over the region, the SAR map determined based, at least in part, on the first RFIM map, providing first RF signals from the plurality of RF coils to the object to induce a nuclear magnetic resonance (NMR) effect, wherein field strengths of the RF signals are varied as a function of location in the region, the spatial variation of the field strengths determined, based at least in part, on the at least one SAR map, and detecting NMR signals emitted from the region as a result of the first RF signals to form, at least in part, first MR data.

Some embodiments of the present invention include an apparatus for obtaining magnetic resonance (MR) and radio frequency impedance mapping (RFIM) data, the apparatus comprising a plurality of radio frequency (RF) coils capable of generating RF signals, an input controller capable providing power to the plurality of RF coils to facilitate generating the RF signals, the input controller configured to power at least some of the plurality of RF coils to provide first RF signals and to power at least some of the plurality of coils to provide second RF signals adapted to obtain RFIM data, an output controller capable of obtaining measurements from the plurality of RF coils, the output controller configured to measure at least some of the RF coils to detect nuclear magnetic resonance (NMR) signals emitted from the region in response to the first RF signals to form, at least in part, first magnetic resonance (MR) data, and to obtain at least one impedance measurement from the plurality of RF coils to form, at least in part, first RFIM data, and at least one computer coupled to the input controller and the output controller to receive data obtained from the plurality of RF coils, the at least one computer configured to compute a first RFIM map indicating the spatial distribution in the region of at least one dielectric property, the first RFIM map computed based, at least in part, on the first RFIM data and the first MR data.

Some embodiments of the present invention include an apparatus for obtaining magnetic resonance (MR) and radio frequency impedance mapping (RFIM) data, the apparatus comprising a plurality of radio frequency (RF) coils capable of generating RF signals, an input controller capable providing power to the plurality of RF coils to facilitate generating the RF signals, the input controller configured to power at least some of the plurality of RF coils to provide first RF signals adapted to obtain the RFIM data, and to power at least some of the plurality of coils to provide second RF signals adapted to induce an NMR effect in the region, an output controller capable of obtaining measurements from the plurality of RF coils, the output controller configured to measure at least some of the RF coils to obtain at least one impedance measurement from the plurality of RF coils in response to the first RF signals to form, at least in part, first RFIM data, and to detect nuclear magnetic resonance (NMR) signals emitted from the region in response to the second RF signals to form, at least in part, first magnetic resonance (MR) data, and at least one computer coupled to the input controller and the output controller to receive data obtained from the plurality of RF coils, the at least one computer configured to compute a first RFIM map indicating a spatial distribution in the region of at least one dielectric property based, at least in part, on the first RFIM data, and to compute a first specific absorption ratio (SAR) map indicating a spatial distribution of SAR values over the region, the SAR map determined based, at least in part, on the first RFIM map, wherein the input controller is configured to vary the field strengths of the second RF signals based, at least in part, on the first SAR map.

DETAILED DESCRIPTION

Figure 1:
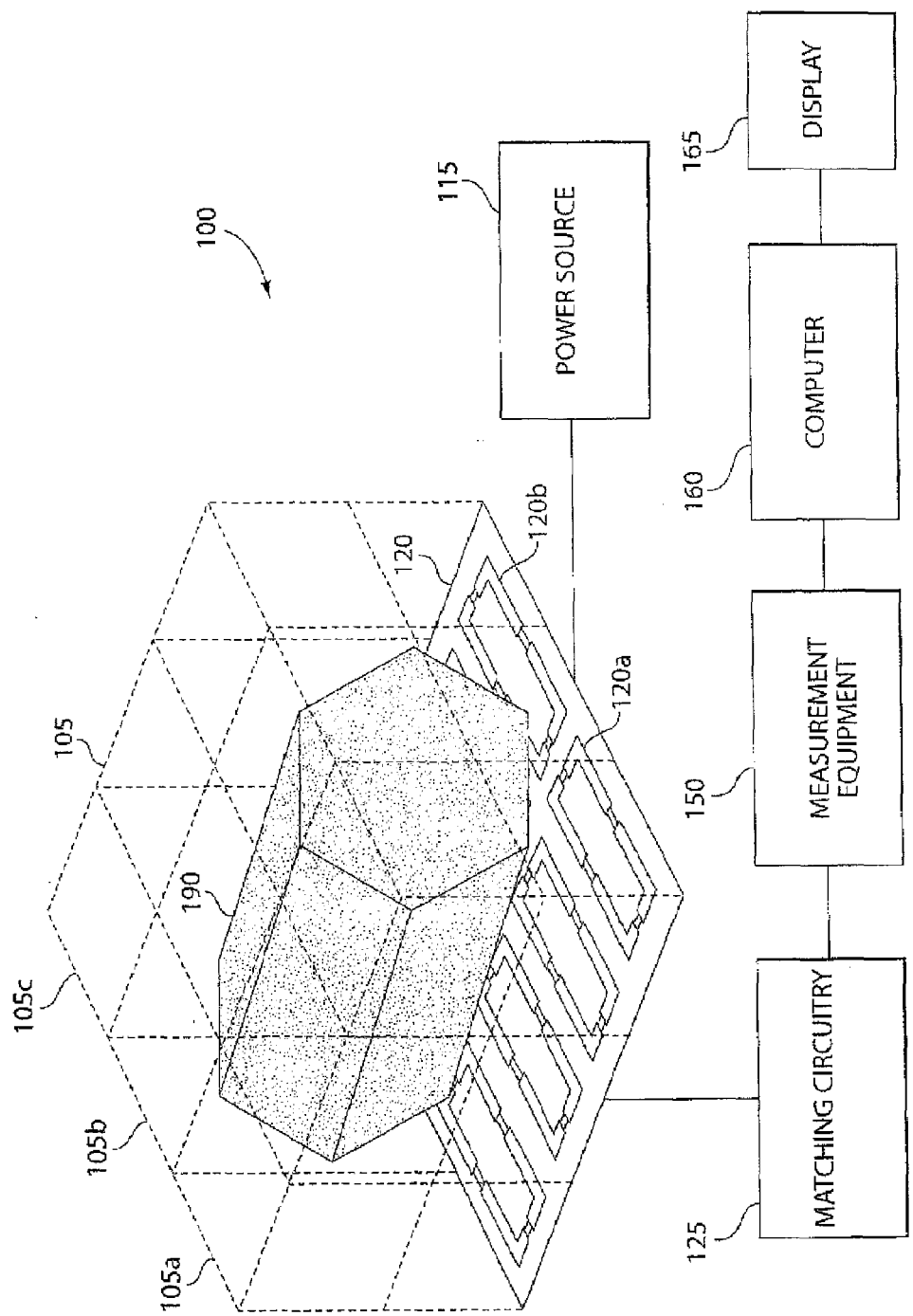
FIG. 1 illustrates an apparatus for obtaining RFIM measurements from a subject to be imaged, in accordance with some embodiments of the present invention.

Various aspects of the present invention derive from Applicant's realization that parallel MR and RFIM may be performed jointly and synergistically within the framework of a shared transmission and reception system using shared RF coils. The information obtained from RFIM measurements may then be used to address one or more outstanding difficulties with parallel MR, for example, difficulties associated with high magnetic field strength. Likewise, the information obtained from parallel MR may also be used to address many of the outstanding difficulties with RFIM. One embodiment according to the present invention includes a new imaging modality and device capable of providing simultaneous and complementary spatially-resolved information about both the MR properties and the dielectric properties of an imaged object.

As discussed above, increasing the magnetic field strength applied during MRI operations (referred to herein generally as high-field MRI) correspondingly increases the baseline signal-to-noise ratio (SNR) of detectable NMR signals emitted from an object being imaged, generally resulting in the potential to produce higher quality, higher resolution images. However, high-field MRI presents various challenges that have conventionally limited the range of clinical applications for high-field MRI. In particular, as the magnetic field strength is increased, the resonant (Larmor) frequency also increases requiring higher frequency RF pulses to invoke the NMR phenomenon.

The increased resonant frequency needed for high-field MRI complicates the process for a number of reasons. First, from a technological standpoint, it is often challenging to achieve uniform RF transmission and reception profiles over large imaging volumes at the increased resonant frequencies associated with high-field MRI. Second, from a biological standpoint, high-field MRI results in increased RF power deposition into biological tissue of the body being imaged. In particular, the deposition of RF power in tissue, known as specific absorption ratio (SAR), increases approximately as the square of the frequency and/or the field strength. As a result, safety limits on SAR may significantly constrain practical application of high-field MRI.

The precise SAR at a region within a body depends, at least in part, on the dielectric properties of the body in the region (e.g., on conductivity, permittivity, and/or permeability values of the tissue in the region). Accordingly, absent a priori information regarding the dielectric properties within the body, the resulting SAR in the region is largely unknown. The situation is complicated by the increased difficulty in achieving uniform RF transmission profiles at high-field strengths. Variation in dielectric properties throughout the body coupled with local focusing of high frequency RF energy can result in highly inhomogeneous distributions of SAR, with significant variations both within a single subject and between subjects. Accordingly, RF power deposition may be limited to levels that are safe for worst case circumstances to avoid depositing harmful levels of RF energy to "hot spots" within the body. As a result of these limitations on RF power, the full benefits of high-field MR may not be able to be realized in clinical in-vivo MRI procedures.

As discussed above, parallel data acquisition increases the speed and efficiency of MRI. However, acceleration of data acquisition in parallel MR results in a corresponding decrease in SNR. Given both the baseline increase in SNR at high field strength and improvements in parallel imaging performance at high frequencies, it has been recognized that high-field MRI may be a significant enabler of parallel MR. At the same time, parallel MR is known to alleviate various known technical limitations and image artifacts associated with high-field MRI. Accordingly, high-field and parallel MR may be used synergistically to improve MRI techniques and procedures.

Thus, there are strong incentives to using parallel MR at high magnetic field strengths. However, conventional attempts to integrate the two technologies have been frustrated by outstanding problems associated with the technologies. In particular, deficiencies in conventional coil sensitivity calibration negatively impacts parallel MR. Coil sensitivity calibration is necessary to characterize the spatial information which may be extracted from any given coil array, and calibration errors remain one of the most common sources of image artifacts in parallel MR. Various techniques for coil sensitivity calibration exist, but none are foolproof. Common problems include the propagation of noise from the calibration into accelerated imaging procedures, and calibration uncertainties in areas of low intrinsic NMR signal. Applicant has appreciated that improvements in the precision and fidelity of coil sensitivity calibration would greatly improve the quality and practical robustness of parallel MR.

As discussed above, another obstacle to high-field MRI includes the safety concerns of RF power deposition at high-field strengths. Applicant has appreciated that mapping of spatial variations of electromagnetic field profiles and/or dielectric properties within a subject may improve parallel MR via improved coil sensitivity calibration, and provide a priori information to guide RF power deposition to avoid harmful exposure to tissue within the body at relatively high-field strengths. Applicant has recognized that at least some of this beneficial information may be obtained using various RFIM techniques.

Accordingly, Applicant has identified the benefit of using RFIM techniques in connection with MRI to provide information about the dielectric properties of the subject to assist in coil sensitivity calibration and/or to provide a map of dielectric properties that can be used to guide deposition of RF power to avoid harmful exposure without having to resort to worst case scenarios that tend to limit RF power levels and correspondingly reduce the resolution and quality of the resulting image.

One fundamental challenge for RFIM is that RFIM image reconstruction is inherently ill-conditioned at appreciable depths within a subject. This results, at least in part, from the inherent smoothness of electromagnetic fields at a distance from current sources (a basic property of Maxwell's equations). As a result of this conditioning issue, the attainment of high spatial resolution is expected to become increasingly difficult with increasing distance from the RFIM array elements. Another challenge is that RFIM reconstruction is computationally intensive, often requiring iterative solutions of Maxwell's equations within a nonlinear optimization algorithm. Reconstructions are currently relatively time-consuming, even when performed on a parallel computer cluster.

Applicant has recognized that information gained from MR measurements may be used to constrain RFIM image reconstruction. In particular, electromagnetic field characteristics can be used as a priori information to condition RFIM optimization schemes. The prior information constrains the optimization and may reduce the chance that the algorithm will converge to a local minimum or other non-optimal solution. In addition, prior information obtained from MR measurements may reduce the computational expense and complexity of RFIM reconstruction. In one embodiment, a priori information obtained from an MR scan converts RFIM image reconstruction to a well-posed problem that can be solved using linear optimization methods, for example, matrix inversion, as discussed in further detail below.

Various aspects of the present invention derive from Applicant's recognition of the benefits of combining MRI and RFIM techniques. In one embodiment, MR measurements are used to assist and/or improve RFIM techniques, and more particularly, to provide prior information to facilitate RFIM computations. In another embodiment, RFIM information is used to facilitate high-field parallel MR techniques. In another embodiment, MR information and RFIM information are used iteratively to improve subsequent MR and RFIM images. In another embodiment, RFIM information is used to provide a SAR map to guide the deposition of RF power into a subject being imaged. In another embodiment, RFIM information is used to assist in coil sensitivity calibration for parallel MR.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

As discussed above, RFIM techniques often employ a plurality of transmit and receive RF coils to determine the dielectric properties of a subject providing a load on the coils. In general, an RFIM system includes a control architecture capable of independent transmission and/or reception along the individual RF coils in the array. For example, FIG. 1 illustrates an exemplary RFIM apparatus 100 including a coil array 120 having a plurality of RF coils (e.g., coil 120a and 120b). Coil array 120 is illustrated as having 8 individual coils. However, the arrangement and number of coils illustrated in FIG. 1 is merely exemplary and is not limiting, as a coil array may be chosen to have any number of coils in any arrangement. For example, a coil array may be arranged such that coils are positioned on all sides or a desired number of sides of an object to be imaged, or above the object instead of just underneath object 190 as shown in FIG. 1.

Power source 115 may be coupled to coil array 120 to provide power to operate the coils. While power source 115 is shown schematically as connected generally to coil array 120, it should be appreciated that the power source may be connected to the coil array such that power (e.g. a voltage or current waveform) may be independently provided to each of the coils in the array, or independently to various subsets of the coils in the array. For example, each coil may have a separate port with which to receive RF wave forms. Power source 115 may be any power component or combination of components capable of providing a set of waveforms to excite the RF coils in a desired fashion.

Coil array 120 may also include various blocking networks that are capable of selectively blocking current flowing around a given coil. Such blocking networks may effectively turn off one or more coils, for example, during calibration or during measurement of other coils in the array, etc. One or more baluns may also be included to prevent unshielded currents from flowing on the cables that connect the array to the other equipment in the system. Other circuitry may be included such that each of the coils in the array (or a selected subset) can be selectively operated. Matching circuitry 125 may also be coupled to coil array 120. As with the power source, matching circuitry is illustrated as generally coupled to the coil array. However, it should be appreciated that each coil may have its own matching circuitry such that various properties of the coil may be measured by measurement equipment 150.

Measurement equipment 150 may be coupled to one or more of the matching circuits to measure properties of the coil array such as a voltage, current and/or impedance of individual coils in the array. Measurement equipment 150 may, for example, include a network analyzer having one or more ports connected to the matching circuitry 125, the network analyzer capable of obtaining measurements of one or more properties of the coil array. In particular, the measurement equipment may be adapted to measure one of more properties of the coil array as a result of exciting the coil array with desired waveforms. A computer 160 may be coupled to the measurement equipment 150 to receive the measurement of one or more properties of the coil array.

Computer 160 may be any component capable of performing mathematic computations and/or logic operations. Computer 160 may be, for example, one or more microprocessors or digital signal processors. Computer 160 may also include a computer readable medium such as a memory capable of being encoded with instructions, for example, a program configured to perform various functions and operations when executed by one or more processors. Computer 160 may be included as part of the measurement equipment 150, for example, a processor included in the network analyzer or may be a separate component. Computer 160 may be configured to perform computations to facilitate operations including, but not limited to, calibrating the coil array, modeling the coil array, computing impedances matrices, forming an image of dielectric properties of a body, etc.

Figure 2:
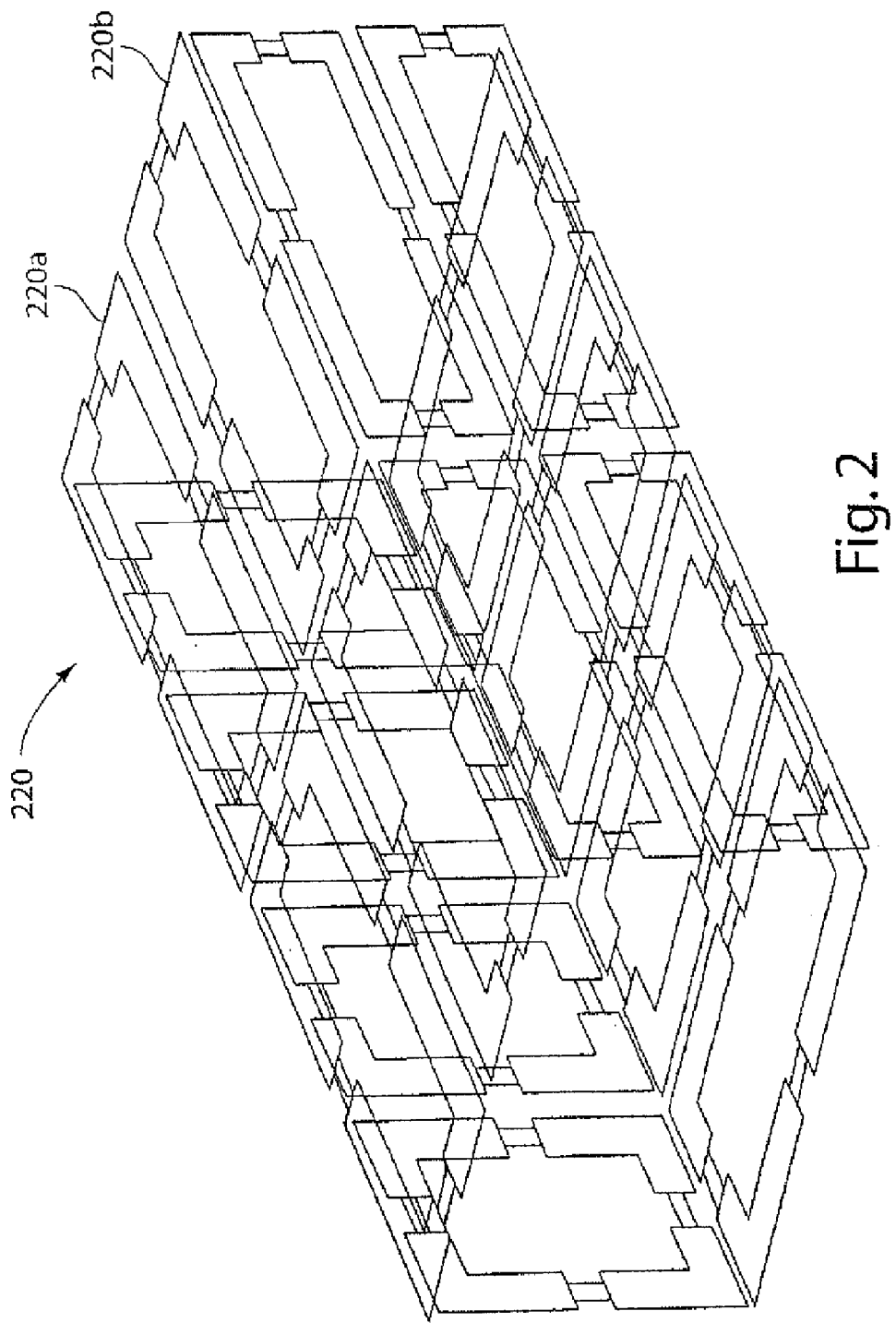
FIG. 2 illustrates an exemplary RF coil array for obtaining RFIM and/or MR measurements, in accordance with some embodiments of the present invention.

FIG. 2 illustrates another embodiment of a coil array in accordance with some embodiments of the present invention. Coil array 220 may be formed from RF coils (e.g., RF coils 220a and 220b) similar to those shown in FIG. 1 and similarly may be connected via multiple transmit and receive channels. Coil array 220 may be particularly well-suited for integration with an MRI device, as the open-ended configuration allows a subject inserted in an MR magnet to be simultaneously positioned within the coil array, as discussed in further detail below. As with the coil array illustrated in FIG. 1, the coils in the array may be independent transmit and receive coils, or may include any depth of parallelism, as the aspects of the invention are not limited in this respect.

It should be appreciated that any configuration of RF coils may be used in a coil array, as the aspects of the invention are not limited in this respect. For example, the sides of the array need not be joined with the top and bottom and can be arranged in any suitable fashion. Further details of methods and apparatus relating to obtaining RFIM information are provided in the '592 application, which is herein incorporated by reference in its entirety. In particular, various methods of obtaining impedance measurements from the RF coil array to facilitate determining electrical properties of the loading body, e.g., by measuring the S-parameters of the RF coil array, are described in the '592 application. However, any method and apparatus for measuring one or more properties of a coil array may be used, as the aspects of the invention are not limited in this respect.

Applicant has appreciated that a coil array adapted to perform RFIM operations shares certain similarities with RF coil arrays used in parallel MR. In particular, the multiple independent transmit and receive channels of RFIM operations are characteristic of parallel MR configurations. Applicant has recognized that RFIM procedures may be performed within an MR magnet using an RF coil array configured to perform both MRI and RFIM functions. For example, any of the RF coil arrays described in connection with FIGS. 1 and 2 (and/or described in the '592 application) may be arranged proximate to an MR magnet and used to obtain both MR and RFIM measurements. An alternate way to view the arrangement is that parallel MR coils designed for MR measurements may also be used to obtain RFIM measurements, as discussed in further detail below.

Figure 3:
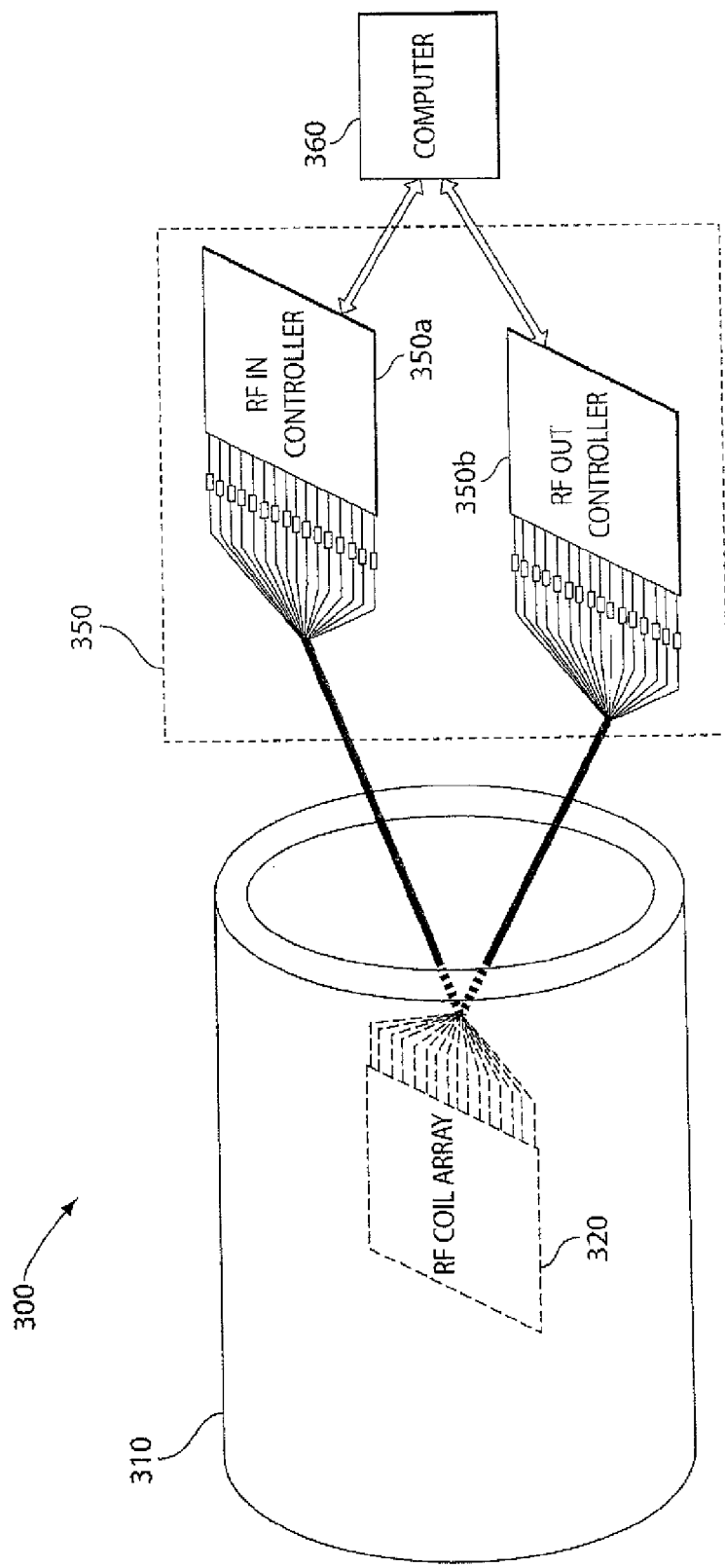
FIG. 3 illustrates a scanner adapted to obtain both RFIM and MR information, in accordance with some embodiments of the present invention.

FIG. 3 illustrates a scanner adapted to perform both MRI and RFIM operations, in accordance with some embodiments of the present invention. Scanner 300 includes a magnet 310 capable of producing a magnetic field of desired strength to align spin properties of molecules of a subject positioned in the interior of the magnet. Magnet 310 may be any of various MR magnets conventionally used in clinical MRI (e.g., approximately 1.5-3.0 T) or may be a high-field magnet (e.g., 3-7 T or higher) and may produce a uniform or gradient magnetic field. Magnet 310 may be of any shape, size and strength and is shown as substantially circular in shape for the purposes of schematic illustration only.

Scanner 300 includes an array of RF coils 320 arranged proximate the magnet and adapted to perform at least some MRI and RFIM operations. RF coil array 320 may be comprised of any number of coils in any configuration. For example, RF coil array may be similar to coil arrays described in connection with FIGS. 1 and 2 and/or similar to coil configurations illustrated in the '592 application. In addition, RF coil array 320 may be configured and operated according to any of the various arrangements and methods described in U.S. Pat. No. 5,910,728 ('728), entitled "Simultaneous Acquisition of Spatial Harmonics (SMASH): Ultra-Fast Imaging with Radiofrequency Coil Array," which is herein incorporated by reference in its entirety.

RF coil array 320 may be an $L(M_t, N_r)$ array where L is the number of coils in the array and $M_t$ and $N_r$ are the number of independent transmit and receive channels, respectively. An independent transmit channel refers to a coupling between RF coils and RF source wherein RF power can be provided to an RF coil coupled to the channel independent of any other RF coil in the array that is not coupled to the same transmit channel. Similarly, an independent reception channel refers to a coupling between RF coils and receiver wherein measurements of one or more properties of the RF coils coupled to the receive channel can be obtained independent of any other RF coil in the array that is not coupled to the same receive channel.

Array 320 is illustrated as a $16(16_t, 16_r)$ array. That is, array 320 has 16 RF coils with 16 independent transmit channels and 16 independent receive channels. Thus, each RF coil in array 320 has its own independent transmit and receive channel. It should be appreciated that array 320 may be of any dimension and include any number of independent transmit and receive channels, as the aspects of the invention are not limited in this respect. In addition, the transmit and receive channels need not share the same level of parallelism. For example, some exemplary coil arrays have configurations including, but not limited to, $64(64_t, 32_r)$, $32(32_t, 1_r)$, $96(64_t, 32_r)$, $16(8_t, 16_r)$, etc. Moreover, coil array configurations need not be arranged in powers of two, as the aspects of the invention are not limited in this respect.

Scanner 300 may further include controller 350 coupled to coil array 320. Controller 350 comprises an RF IN controller 350a and an RF OUT controller 350b. RF IN controller 350a is adapted to provide and control RF power to the RF coils in the array. In particular, RF IN controller 350a is configured to provide RF power across the M independent transmit channels to respective coils in the array. Similarly, RF OUT controller 350b is adapted to measure one or more properties of the RF coils over the N independent reception channels in the array. Controller 350 may be a network analyzer or a custom made controller adapted to transmit RF power to and obtain measurements from coil array 320.

A computer 360 may be coupled to controller 350, either connected to RF IN controller 350a, RF OUT controller 350b, or both. Computer 360 may include one or more programs configured to process information received from the controller 350. For example, computer 360 may be configured to perform image reconstruction based on measurements received from RF OUT controller 350b, various optimization algorithms and/or other computations that process information obtained by, or to be provided to, controller 350. Computer 360 may include one or more programs configured to control the synchronization of controller 350 and/or control the sequencing of various operations performed by scanner 300, as discussed in further detail below. Computer 360 may be configured to control the characteristics of various pulse sequences used to excite the coils, for example, any conventional or unconventional pulse sequences used to invoke the NMR effect.

Scanner 300 may be adapted to obtain both MR and RFIM information. In particular, scanner 300 may be configured to operate as a parallel MR scanner (or in some embodiments, a non-parallel MR scanner). RF IN controller 350a may be adapted to provide RF power to the RF coils at customary power levels for MR protocols, at resonant frequencies consistent with the magnetic field strength of the selected magnet 310, using any of various standard or non-standard RF pulse sequences adapted to invoke the NMR phenomenon. Array 320 may be arranged within the magnet in any configuration traditionally used in MR scanners, or any configuration that facilitates performing MR operations, conventionally or according to any parallel MR configuration, as the aspects of the invention are not limited in this respect.

When performing MR operations, controller 350 may use less than all the available independent transmit and receive channels. For example, RF IN controller 350a may provide RF power over m<=M independent channels. Similarly, RF OUT controller 350b may receive measurements over n<=N channels. Moreover, controller 350 may use some, all, or a subset of the RF coils in performing MR operations. For example, controller 350 may utilize l<=L RF coils during MR operations. Accordingly, array 320 may be used as an $l(m_t, n_r)$ array of any desired combination of l, $m_t$ and $n_r$ when scanner 300 is being operated for purposes of obtaining MR information by appropriately configuring controller 350. Controller 350a may be configured to transmit any desired RF pulse sequence to array 320 to invoke the NMR phenomenon at any desired level of parallelism. Similarly, controller 350b may be configured to obtain NMR signals at any desired number of coils in the array to acquire MR measurements.

Scanner 300 also may operate as an RFIM device. In particular, RF IN controller 350a may be adapted to provide RF power to array 320 and RF OUT controller 350b may be adapted to measure one or more properties and/or load characteristics (e.g., coil impedance) to obtain information about the spatial variation of one or more dielectric properties (e.g., conductivity, permittivity, permeability, etc.) of the subject positioned in the scanner. As with MR operations, any number of RF coils may be used to perform RFIM operations, either independently or together in any combination to form an l'(m$_t$',n$_r$') array to obtain RFIM information. Accordingly, the same coil array may be utilized to obtain both MR and RFIM information. It should be appreciated that the same number of coils need not be used for RFIM and MR operations, nor does the same level of parallelism need to be achieved. Accordingly, controller 350 may be adapted to use more, less or the same number of independent transmit and receive channels for RFIM as for MR operations.

RF IN controller 350b may be configured to provide RF power at any strength during RFIM operations. For example, different RF power levels may be used for MR operations and RFIM operations. In general, lower power RF signals are transmitted to the coils for RFIM operations than for MR operations, although this is not a limitation on the aspects of the invention. Accordingly, RF IN controller may include one or more programs, implemented in hardware, software or a combination of both, that provide RF power to array 320 at the appropriate power levels and the appropriate sequences for both MR and RFIM operations. Similarly, RF OUT controller 350b may include one or more programs, implemented in hardware/software that obtain measurements from array 320 as suitable for MR and RFIM operations. For example, when performing MR operations, controller 350b may be configured to detect NMR signals emitted from the subject. When performing RFIM operations, controller 350b may be configured to measure coil impedances. Alternatively, programs controlling sequencing, synchronization and power levels may be implemented on computer 360, which may then instruct RF IN controller 350a and RF OUT controller 350b, accordingly.

Figure 4:
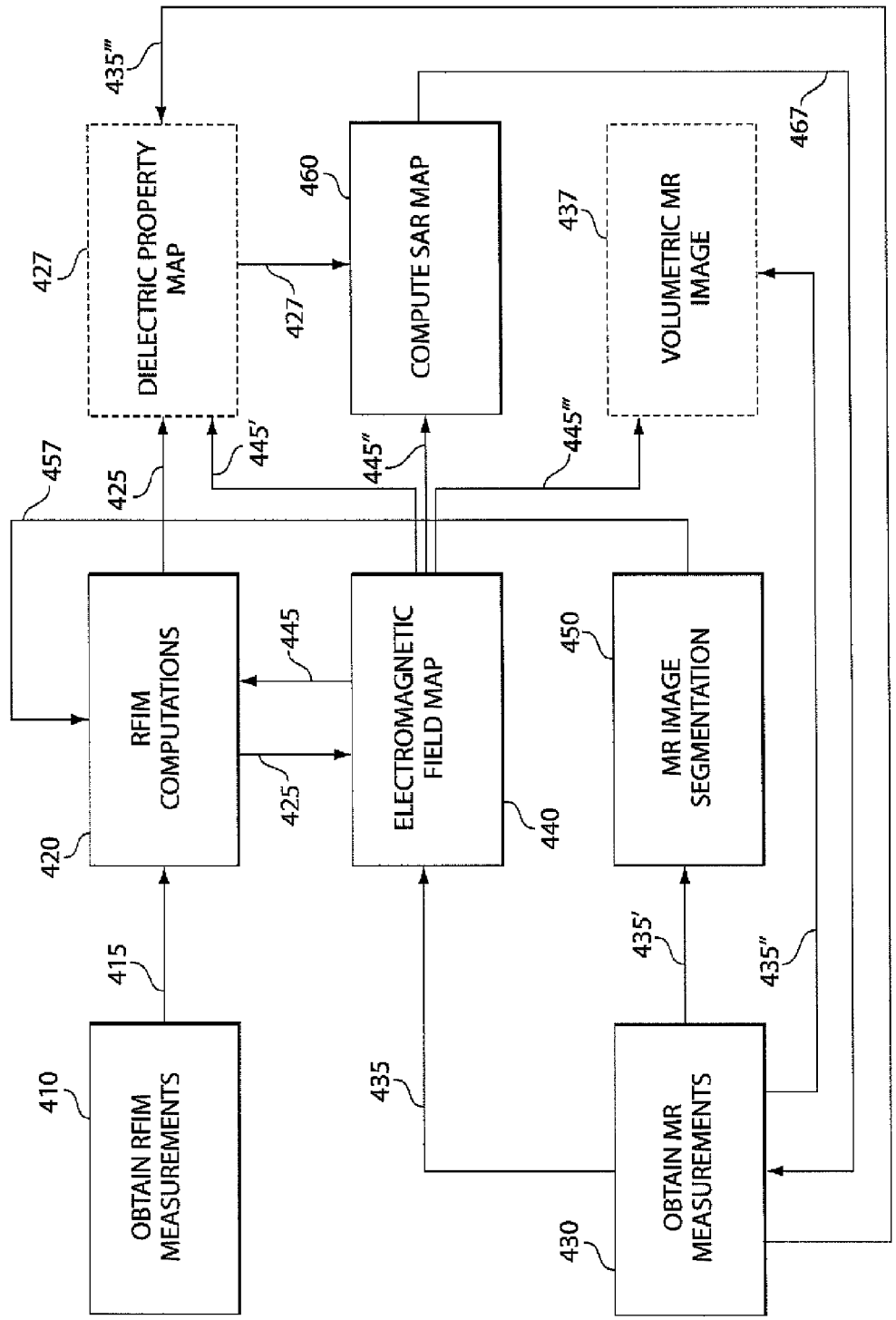
FIG. 4 illustrates a diagram of various operations utilizing RFIM and MR information, in accordance with various embodiments of the present invention.

As discussed above, Applicant has identified various methods by which MR and RFIM information may be used together to improve the performance, quality, resolution and/or safety of MR and/or RFIM operations. For example, Applicant has developed methods that may be performed by scanner 300 to obtain MR and RFIM information that can be used together to improve upon the quality of the information that could be obtained from either modality independently. FIG. 4 illustrates various operations that exploit one or more synergies existing between the two modalities. However, the methods described below are merely exemplary. MR and RFIM information may be combined, integrated and/or used together in any manner, as the aspects of the invention are not limited in this respect.

FIG. 4 is a diagram illustrating various MR and RFIM techniques that can be used in any combination, in accordance with various embodiments of the present invention. The various techniques, for example, may be implemented on a device such as scanner 300 that share, to some extent, one or more transmission and reception channels for MR and RFIM operations. However, the methods described below may be performed by other devices implemented in any way suitable for obtaining MR and RFIM information, as the aspects of the invention are not limited for use on any particular device and/or limited to any particular implementation.

In act 410, RFIM measurements may be obtained for an object being imaged. In particular, act 410 may include providing RF power to one of the RF coils and measuring the resulting impedance at the other RF coils in the absence of the load. In addition, the impedance of the coil to which RF power is provided may be measured. This operation may be repeated at each successive independent RF coil to obtain a calibration measurement of the RF coil array without the influence of a load. The object to be imaged may then be placed proximate the coil array and the procedure of applying RF power to each coil and measuring the response in the other coils (and/or in the coil to which power is applied) may be repeated to obtain information about dielectric properties of the object being imaged. The effect on the RF coils due to the loading object may be used to characterize the spatial variation of one or more dielectric properties within the object, providing RFIM measurements 415.

In one embodiment, the response measured in the RF coils includes measuring the impedance in each coil (e.g., measuring $Z_{ij}(\omega)$ as shown in Equation (1) below) that results from applying RF power to one or more of the other RF coils. The impedance effects on the array, when perturbed by the loading body (i.e., the object being imaged), encodes information about the variation of dielectric properties within the object. As discussed in the '592 application, the basic operating equation for RFIM computations may, according to some embodiments, be expressed as, $$Z_{ij}(\omega) = \int_V \left\{ \begin{array}{l} \sigma(\vec{x},\omega)\vec{E}_i^*(\vec{x},\omega)\cdot\vec{E}_j(\vec{x},\omega) - \\ i\omega \left[ \begin{array}{l} \varepsilon(\vec{x},\omega)\vec{E}_i^*(\vec{x},\omega)\cdot\vec{E}_j(\vec{x},\omega) - \\ \mu(\vec{x},\omega)^{-1}\vec{B}_i^*(\vec{x},\omega)\cdot\vec{B}_j(\vec{x},\omega) \end{array} \right] \end{array} \right\} + \int_S \vec{E}_i^*(\vec{x},\omega)\times\vec{B}_j(\vec{x},\omega)\cdot d\vec{S} \quad (1)$$

where $Z_{ij}(\omega)$ is the measured impedance at frequency $\omega$ of the $i^{th}$ coil in response to operating the $j^{th}$ coil in an L-coil array. $\vec{E}_i(\vec{x},\omega)$ and $\vec{B}_i(\vec{x},\omega)$ denote, respectively, electric and magnetic fields resulting from a unit current in the $i^{th}$ coil of the array. The electrical conductivity $\sigma(\vec{x},\omega)$, electrical permittivity $\varepsilon(\vec{x},\omega)$, and magnetic permeability $\mu(\vec{x},\omega)$ are the dielectric properties of interest, and the vector $\vec{x}$ is a direction of the one or more axes over which these properties may vary.

As discussed above, RFIM measurements may be obtained in the absence, and then in the presence, of the load. To obtain further RFIM information, the architecture of the scanner may be used to advantage. For example, some scanner implementations may include a moveable table (e.g., a patient table) that transports the subject within the magnet and positions the subject proximate the coil array. Rather than performing coil loading measurements only in the absence of the load and once with the subject fully positioned within the device, loading measurements at multiple spatial positions may be obtained as the subject is inserted in a controlled fashion into the scanner.

Such an approach would provide additional known spatial modulations of the volume integral in Equation (1), e.g., with the spatial position $\vec{x}$ within the integral shifted to $\vec{x}+\Delta\vec{x}_k$, where $\Delta\vec{x}_k$ is the spatial offset at each step k of the moveable table trajectory. These modulations provide additional information that may be used to improve the characterization of dielectric properties within the subject, and to improve the spatial resolution of obtained dielectric properties (e.g., resulting images and/or dielectric property maps of the subject). However, RFIM measurements 415 need not include this additional information and may be obtained in any manner.

In act 420, RFIM measurements 415 obtained during act 410 are used to compute one or more maps (e.g., dielectric property map 425) of one or more of the dielectric properties of the object being imaged. The term "map" refers herein to any indication of the spatial distribution of one or more properties. For example, a map may include scalar and/or vector values as a function of location in space, wherein the values are indicative of some property such as electromagnetic field components, dielectric properties, NMR signal strengths, SAR, etc. A map may take the form of a two or three dimensional image for visualization, or may be stored in other forms, as the aspects of the invention are not limited in this respect.

As discussed in the '592 application, one method of performing RFIM computations includes generating a model of the spatial variation of one or more dielectric properties, and instantiating the model with an initial guess of dielectric property values. The loading effect (e.g., impedance values at each of the coils) that would result from the modeled spatial distribution of dielectric properties may be computationally simulated and compared to the actual RFIM measurements taken from the RF coil array. The modeled spatial distribution of dielectric properties may then be iteratively adjusted until the simulated impedance measurements of the coil array are closest (according to some nearness measure) to the actual measurements obtained.

The term "model" refers generally to a description or representation of one or more objects (e.g., a coil array, an imaging volume and its contents, such as a body to be imaged, etc.). While a model may emulate a real object (e.g., a model of coil array may have a real coil array counterpart), a model is virtual, and typically embodied by one or more mathematical descriptions. For example, a model may include descriptions of the geometry of the one or more objects and/or a uniform or arbitrary grid superimposed on the object, parameters that describe the characteristics of the object, and/or environment, etc. Models may be stored electronically, for example, on computer memory or as part of an executable program stored on computer memory.

In order that a model emulate at least some properties of the real environment, one or more functions of the environment being modeled may be simulated using the model representation. Simulation refers to computing a function, operation or action such that the model representation behaves similarly to its real counterpart. Consider the case when the real objects being modeled include a coil array. When one or more coils in the array are operated, electromagnetic fields are generated. This electromagnetic environment in turn affects properties of the coil. Simulation of a coil array model may include computing the electromagnetic environment of the coil array either in the presence or absence of a body acting as a load. Methods and algorithms for performing a simulation are often embodied in one or more software programs operating on the model or representation of the system being simulated. For example, a model of a coil array may be simulated by solving Maxwell's equations within an imaging volume defined as part of the model.

One method of simulating a model of a coil array (both with and without a load) includes solving Maxwell's equations according to a Finite Difference Time Domain (FDTD) algorithm. In FDTD, a volume of space (e.g., the imaging volume) with or without one or more objects (e.g., a body to be imaged) is partitioned into a lattice or mesh. The electromagnetic fields in each region of the mesh are solved for according to an applied set of initial conditions (e.g., conductivity and/or permittivity distribution, coil geometry, etc.) and boundary conditions (e.g., the extent of the imaging volume, etc.). While FDTD may provide a fast and effective method for simulating the operation of a coil array and computing an impedance matrix, any of various other computational methods including Chebyshev polynomial expansion, finite element, finite difference frequency domain (FDFD) algorithms, any of various other frequency domain computational methods etc., may be suitable for simulation and are considered to be within the scope of the invention.

However, modeling techniques or other non-linear optimization schemes are computation intensive and may be vulnerable to converging to local minimums or other non-optimal solutions. As shown in Equation (1), in the absence of any a priori information, both the electromagnetic fields and the dielectric properties are unknown, and are therefore, according to some embodiments, generated through the relatively intensive electrodynamic modeling process described above. Moreover, the optimization algorithm may guide the spatial distribution of dielectric properties to a local minimum that may not be highly reflective of the actual spatial distribution of dielectric properties of the object being imaged. Accordingly, without any prior information, the dielectric property map 425 resulting from RFIM computations 420 may be relatively expensive to generate and sub-optimal in result.

Applicant has recognized that if the E and B fields are known, their values specify a linear relationship between the measured impedances on the one hand and the dielectric property values on the other. Therefore, information about the E and B fields can greatly reduce the complexity of, and in some cases linearize, RFIM computations. Applicant has recognized that such E and B field information may be obtained from MR measurements. In some embodiments, a single matrix inversion procedure may be used to extract one or more dielectric property values from the electromagnetic field components obtained from MR measurements without the need for generally computationally expensive optimization schemes that may generate non-optimal solutions.

For example, writing the values $Z_{ij}(\omega)$ as the elements of a vector Z, the values $\sigma(\vec{x},\omega)$, $\in(\vec{x},\omega)$, and $\mu(\vec{x},\omega)^{-1}$ at various spatial positions (and, perhaps, various frequencies) as elements of an unknown property vector P, grouping the obtained electromagnetic field values at various positions into an appropriately configured encoding matrix E, and collecting additive terms (such as the final surface integral in Equation (1) and/or the permeability term if permeability is to be assumed constant) into an additive vector $Z_0$, Equation (1) can be rewritten as, $$Z = EP + Z_0 \qquad (2).$$

This matrix equation may be solved using standard linear algebraic methods, avoiding both the electrodynamic modeling and the nonlinear optimization of the RFIM reconstruction described above. Applicant has recognized that the E and B fields, in part or in whole, may be obtained from MR measurements. Electromagnetic field measurements obtained from MR measurements may be used as prior information to inform and constrain RFIM computations to decrease the complexity of the computation and/or reduce the chances of converging to a local minimum. As discussed above, MR measurements may, in some cases, convert RFIM computations into a linear inverse problem.

In act 430, MR measurements may be obtained, for example, by operating scanner 300 according to any of various available MR techniques. In particular, the MR magnet (e.g., magnet 310) may produce a homogenous and/or gradient magnetic field at a desired field strength and the RF coils (e.g., RF coils in array 320) may be operated to generate pulses at the appropriate frequency and according to a desired pulse sequence to induce the NMR phenomenon, which may, in turn, be detected by the RF coils. Accordingly, MR measurements 435 may include NMR signal strengths detected from the object being imaged. MR measurements may be obtained using single or parallel data acquisition techniques, as the aspects of the invention are not limited in this respect. That is, one or more independent transmit and/or receive coils may be used to obtain MR measurements 435. However, some level of parallelism may be preferable to fully exploit some of the synergies recognized by Applicant, as discussed in further detail below.

As discussed above, Applicant has recognized that electromagnetic field information available from MR measurements may be used to provide a priori information beneficial to RFIM computations. In act 440, one or more electromagnetic field maps of the object being imaged may be generated using MR measurements 435, and/or electrical properties 425 determined from RFIM computations 420.

MR measurements have been used in the past to obtain at least some electromagnetic properties. In particular, MR measurements have been used to map RF transmission profiles. These so-called "$B_1$ profiles" may be useful in characterizing inhomogeneities in RF transmission (particularly at high magnetic field strengths where it becomes increasingly difficult to generate homogenous RF transmissions). However, traditional $B_1$ field mapping techniques, e.g., using multiple measurements with RF pulses of different amplitude, derive only the magnitude of one circularly polarized component of the RF magnetic field perpendicular to the main magnetic field $B_0$ (e.g., the magnetic field generated by magnet 310).

The direction or phase of the $B_1$ field, or, alternatively, the relative amplitudes and phases of its two transverse components, are typically unavailable using conventional techniques. However, to best assist RFIM computations, the full set of magnetic field components as a function of position in the subject is desirable, though not necessarily required. This information may be gleaned from independent measurements of transmission and reception at a plurality of coils in the array. In particular, information obtained from inter-comparison of measurements made during transmission and reception in different coil elements of a coil array may be useful in extracting the necessary amplitude and phase information. Accordingly, parallel MR facilitates the determination of electromagnetic field components that in turn benefit RFIM computations. That is, MR measurements 435 obtained using parallel MR techniques (e.g., multiple independent transmit/receive channels) encode information from which electromagnetic field components may be determined.

The field mapping procedure described above results in, for each array element, values of the two independent components of the RF magnetic field perpendicular to the main magnetic field $B_0$. To further facilitate RFIM reconstruction by achieving full linearization, all three spatial components of the magnetic field and the electric field may be obtained. If only two components of the magnetic field are known, the third component may be generated using the constraint, $$\vec{\nabla} \cdot \vec{B} = 0 \quad (3).$$

Appropriate spatial integration of the two known components may be used to determine the missing third component. More particularly, the constraint provided in Equation (3) may be used to determine the third component up to an additive constant. This constant may be determined by using the physical requirement that the coil's magnetic field vanish at large distances from the coil. Alternatively, it would be possible to overlay a DC path onto the RF coil array and measure the perturbations in the phase of the MR magnetization that result from application of short DC current pulses to the coils. This would provide a direct measure of the longitudinal component of the coil magnetic field. With the three components of the B-field obtained, the three E-field components may be determined. A number of approaches for E field determination are possible, taking advantage of the relations between E and B-fields as specified by Maxwell's equations. For example, spatial integration of the expression of Faraday's Law, $$\vec{\nabla} \times \vec{E} = -\partial \vec{B}/\partial t = -i\omega \vec{B} \quad (4)$$

(where the final equality results from assuming harmonic time-variation in the RF magnetic fields) yields the three components of E, at least up to a "conservative" component which may be expressed as the gradient of a scalar, and which vanishes on the left hand side of Equation (4). Accordingly, electromagnetic field components may be obtained from MR measurements to constrain and/or linearize RFIM computations. Another approach would involve calculation of E from derivatives of B, for example, by virtue of the expression, $$\vec{\nabla} \times \vec{B} = \mu \vec{J} + \varepsilon\mu \frac{\partial \vec{E}}{\partial t} \approx \mu(\sigma + i\omega\varepsilon)\vec{E}. \quad (5)$$

However, using Equation (5) would also require at least approximate estimates of the unknown electrical parameters σ, ∈, and μ. Components of the electric and magnetic fields based on MR measurements may be obtained in other ways, as the aspects of the invention are not limited in this respect. Applicant has appreciated that the estimates of electrical parameters may be obtained via unassisted RFIM computations. In particular, dielectric properties σ, ∈ and μ may be determined in act 420, for example, using any available optimization technique, such as electrodynamic modeling as described above. The dielectric parameters 420 may then be used to determine electromagnetic field components, e.g., according to the expression in Equation (5). The computed electromagnetic field components may then be used to constrain further RFIM computations (e.g., by performing act 420 again with electromagnetic field properties determined in act 440). In this way, initial estimates of one or more dielectric properties may be used to bootstrap further computations to improve RFIM results.

It should be appreciated that some of the field mapping procedures described above rely on two field components (i.e., the two transverse magnetic field components), and that, as a result, noise and error propagation may be unfavorable in some situations. However, even if all field components are not fully characterized to achieve full linearization, the one or more electromagnetic field properties that can be obtained from MR measurements can be used to constrain the nonlinear RFIM and thereby reduce computation time and effort. For example, taking the curl of both sides of Equation (5) results in the expression, $$\vec{\nabla} \times (\vec{\nabla} \times \vec{B}) = \vec{\nabla}(\vec{\nabla} \cdot \vec{B}) - \nabla^2 \vec{B} \quad (6)$$

$$= -\nabla^2 \vec{B}$$

$$= \vec{\nabla}(\mu(\sigma + i\omega\varepsilon)) \times \vec{E} + \mu(\sigma + i\omega\varepsilon)\vec{\nabla} \times \vec{E}$$

$$\approx \mu(\sigma + i\omega\varepsilon)\vec{\nabla} \times \vec{E}$$

$$= -i\omega\mu(\sigma + i\omega\varepsilon)\vec{B}$$

or $$\nabla^2 \vec{B} = i\omega\mu(\sigma + i\omega\varepsilon)\vec{B} \quad (7)$$

Accordingly, any electromagnetic field information obtained from MR measurements may be used to constrain and/or condition RFIM computations to reduce the complexity and computation time and/or reduce the chance that a selected optimization scheme will converge to a local minimum or other non-optimal solution. The above derivations of Maxwell's equations are merely exemplary methods of determining one or more electromagnetic field components and/or dielectric properties. Other methods may be used, as the aspects of the invention are not limited in this respect.

Applicant has further appreciated that Equation (7) also represents a method of estimating electrical properties directly from the measured magnetic field maps alone. For example, one may take the second derivative of any component of the measured B field at each spatial position and divide by the value of the same field component to derive $\sigma$ and $\in$, if $\mu$ is held fixed. It should be appreciated that the gradient operator, acting on the conductivity and permittivity in the second line of Equation (6), has been neglected in the approximation shown in third line. However, in homogeneous regions of the body (as may be determined, for instance, using segmentation techniques described below), the approximation is correct and provides a means of determining local dielectric properties, and various mathematical procedures may be derived to estimate corrections near edges (e.g., regions of relatively rapidly changing dielectric property values). Accordingly, magnetic field components determined from MR measurements may be used to estimate dielectric properties, either directly from MR measurements 435 or via electromagnetic field map calculations (e.g., via act 440).

It should further be appreciated that the correct application of Equations 6 and 7 for electrical property mapping may require knowledge of the full complex magnetic field components, including both magnitude and phase. As discussed above, information from multiple coil array elements may be useful in determining this information.

The dielectric property estimates obtained directly from MR measurements may be used to verify RFIM results and/or to provide an independent measurement of dielectric properties of the subject. In addition to using electromagnetic field maps 445 obtained from MR measurements and/or dielectric parameters determined from RFIM computations to assist in RFIM computations, and to directly compute dielectric properties, electromagnetic field maps 445 may assist in generating SAR maps to increase the safety of high-field MR, as discussed in further detail below.

Applicant has appreciated that region characterization available from MR images may further assist RFIM computations. In act 450, an MR image may be segmented into like regions. The term "segment" or "segmentation" refers herein to grouping pixels or voxels within an image according to some desired measure. For example, an image may be segmented by grouping connected pixels or voxels with similar intensity values into a labeled region. Segmentation may be performed either automatically via a segmentation algorithm, or manually by having an operator select the segmented regions, or a combination of both. Numerous segmentation methods are known and available and any segmentation method may used, as the invention is not limited in this respect.

In one embodiment, an MR image is segmented to identify generally like regions in the image. For example, an MR image of the human body may be segmented to indicate generally homogenous regions associated with particular organs or regions of like tissue. The segmented regions may then be used to constrain RFIM computations. For example, the segmented regions of MR image 457 may be used to instruct the computations performed in act 420 as to the locations of generally homogenous regions in the image and/or to the specific locations of identified pathologies. Moreover, the segmentation information may be used to identify homogeneous regions, which validate assumptions made in computations based on the approximation in Equation (6). That is, segmentation information facilitates computations of one or more dielectric properties from electromagnetic field maps as expressed in Equation (7), which relies on the approximation in Equation (6).

The availability of segmentation information obtained from one or more MR images of the body also allows intelligent choice of pixel or voxel shapes and positions for RFIM, to improve the conditioning of RFIM computations. In particular, the MRI image may be segmented to differentiate distinct organs or tissues, and pixels or voxels may be chosen to reflect actual anatomy, rather than to lie on an arbitrary grid (as is typically done in conventional image reconstruction). The use of a small number of target voxels chosen based on the segmentation may reduce the number, and in many cases, increase the size of regions needed to adequately characterize the body, providing a better intrinsic fit to the smooth electromagnetic fields underlying RFIM.

Further improvements may also be applied specifically for the investigation of pathology. In addition to using organ- or tissue-based segmentation (whether automatically, or manually with user input) regions of suspected pathology in the MR images may be identified. Standard values may then be used for surrounding tissue, allowing only the properties for the identified regions to "float" freely. Since the reconstruction problem in such a situation will be significantly more constrained than the general RFIM reconstruction problem, it may avoid many difficulties with conditioning. It should be appreciated that MR image segmentation information may be used alone or in combination with electromagnetic field information obtained from the MR measurements, as the aspects of the invention are not limited in this respect.

The information obtained from MR measurements (e.g., electromagnetic field information, segmentation information, etc.) may be used to facilitate RFIM computations and substantially improve resulting dielectric property maps 427. In a complementary fashion, the dielectric property maps that result from RFIM operations (and/or computed directly from electromagnetic field maps) can themselves be used to improve MRI. In one embodiment, RFIM electrical property maps may be used to guide RF power deposition in MR operations by identifying SAR values within a subject based on the dielectric properties determined from RFIM.

As discussed above, SAR has been identified as an increasingly important consideration in high field MRI. SAR is closely related (by a reciprocity principle) to the first term in the integrand of Equation (1), and may be calculated if values of electric field, conductivity, and/or permittivity (which affects the electric field distribution) are known at various points within a body. In act 460, maps of σ and ∈ (e.g., as determined in act 420), in combination with the electromagnetic field information 445' (e.g., as determined in act 440), may be used to generate SAR values throughout a subject being imaged. The use of primes (') in connection with the same reference numeral herein denotes that the information is obtained from the same general operation or act, but may be of different content and/or format, or may have undergone or been omitted from additional processing upon generation.

As discussed above, conventional methods of handling problems associated with RF power deposition due to generally unknown SAR variation typically involve treating each subject as the worst case scenario with respect to SAR. That is, despite the substantial SAR variation from individual to individual and from region to region within a single individual, power levels must be lowered to the least common denominator to avoid depositing harmful levels of RF radiation at certain locations in the body (e.g., hot spots). Accordingly, the benefits of high field MRI often cannot be utilized in clinical settings because of the dangers of RF power deposition.

Applicant has appreciated that one or more SAR maps (i.e., the spatial variation and/or distribution of SAR with respect to the subject being imaged) may be generated using one or any combination of dielectric property information (e.g., dielectric property map 427) determined from RFIM computations, electromagnetic field information (e.g., electromagnetic field information 445'') obtained from MR measurements (with or without RFIM measurements), segmented MR images, or computed directly from MR measurements.

A SAR map may be computed from dielectric properties provided by dielectric property map 427. In particular, since locations in space have been assigned values for one or more dielectric properties, a SAR value may be computed at the corresponding location based on the determined dielectric properties. The SAR map, in turn, may operate as a guide during subsequent MR operations. For example, SAR map 467 may be used to instruct an operator with respect to safe levels of RF power deposition at various locations within the subject being imaged. Since SAR levels have been computed and are therefore known, the worst case scenario can be dispensed with in favor of tailoring RF power deposition according to SAR map indications. MR images guided by one or more SAR maps may then benefit from the increased SNR of high-field MR to generate higher resolution and/or better quality MR images. As discussed above, parallel MR facilitates delivering different power levels to different regions of an object due to its spatial selectivity, making parallel MR techniques particularly advantageous in this respect.

In addition to monitoring and controlling SAR in individual subjects to, for example, provide safety assurance in high-field MRI, SAR distributions may be used to characterize subject-to-subject variation, verify existing computational models and/or evaluate new pulse sequences and coil designs. Even without the full information on the dielectric properties of a subject (e.g., as provided by RFIM), electromagnetic field maps (alone or in combination with segmented MRI data using standard electric properties for each tissue type) may be used to obtain estimates of local SAR. Moreover, with obtained SAR maps, parallel RF transmit profiles may be adjusted to reduce SAR, to improve signal homogeneity, etc. In embodiments that include a parallel transmit-receive system, multi-port transmit techniques, guided by SAR maps, may improve the safety, robustness, and quality of MRI at high field strength.

Parallel MR imaging may benefit not only from the availability of multiple receiver channels, but also from the availability of comprehensive electromagnetic field maps. Traditional coil sensitivity maps for parallel imaging track the amplitude and phase of one circularly polarized magnetic field component (or, equivalently, a particular linear combination of two Cartesian components). This information may already be available from the field mapping procedures described earlier. In other words, a single unified calibration procedure may provide all the information required both for sensitivity calibration and for more extensive field mapping.

In addition, with the full complement of field components and dielectric properties available, one may be able to use Maxwell's equations to extend coil sensitivities into 'gaps' that may occur in regions of low signal, and possibly to reduce noise in sensitivity maps. Even in the absence of detailed field mapping, the coil loading measurements associated with RFIM may yield practical benefits for MRI. For example, the loading measurements obtained from RFIM may be used to readjust the tuning and matching of coils interactively for improved SNR in the presence of a particular subject, as discussed in further detail below.

The adjusted parallel transmit profiles, improved coil sensitivities and computed SAR maps obtained from dielectric properties and/or electromagnetic field information may be used to improve subsequent MR measurements. In one embodiment, the improved operating characteristics of the scanner (e.g., adjusted transmit profiles and improved coil calibration) in connection with tailored RF deposition afforded by SAR maps (e.g., to facilitate high quality high-field MR) are employed to obtain MR measurements which may then be reconstructed to form volumetric MR image 437. The improved MR conditions facilitate acquiring higher resolution, higher quality images as well as enabling relatively fast and efficient parallel MR operations, which in turn may improve the spatial resolution of the resulting MR images.

FIG. 4 illustrates various exemplary operations that take advantage of one or more synergies that Applicant has identified between MRI, RFIM and parallel MR. The various acts illustrated in FIG. 4 can be used in any number of combinations to facilitate MRI, parallel MR and/or RFIM imaging modalities. Several exemplary combinations of MR and RFIM operations are described below in connection with FIGS. 5-9. Other combinations of integrating MR and RFIM information may also be used, as the aspects of the invention are not limited in this respect.

Figure 5:
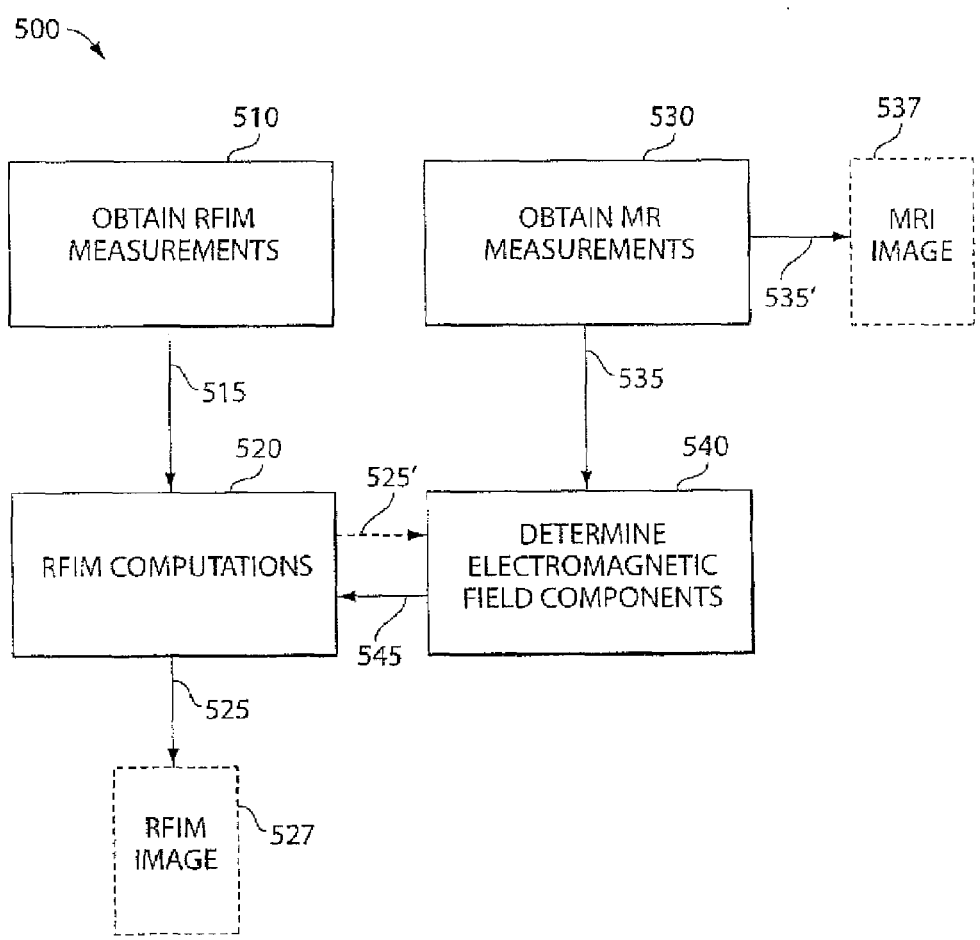
FIG. 5 illustrates a method of combining RFIM and MR information, in accordance with some embodiments of the present invention.

FIG. 5 illustrates a method 500 of integrating MR and RFIM measurements, in accordance with some embodiments of the present invention. It should be appreciated that the following methods may be performed on a dual-mode scanner such as scanner 300 described in connection with FIG. 3, or any other device capable of acquiring MR and RFIM information. In act 510, RFIM measurements are obtained. For example, the RF coils in the array may be operated to obtain RFIM measurements in the absence of the load. A patient to be imaged may then be positioned on a moveable table, or other conveyance means, and inserted inside a suitable MR magnet.

The RFIM coils in the array may then be operated again to obtain RFIM measurements in the presence of a load (e.g., the patient). The RFIM measurements may be obtained either after the patient has been positioned fully within the scanner, or multiple RFIM measurements may be progressively taken as the patient is inserted into the scanner. The RFIM measurements in the absence of the patient, and the one or more measurements in the presence of the patient may be appropriately compared to provide RFIM information 515 indicative of the dielectric property distribution within the patient.

In act 530, MR measurements are obtained. Any type of MR scan may be performed to obtain information indicative of the NMR signal variation emitted from the patient to obtain MR measurements 535. Some or all of the MR measurements (e.g., MR measurements 535') may be used in a reconstruction process to form an MRI image 537 of the internal structure of the patient. It should be appreciated that MR measurements may be obtained by a parallel MR scanner of any order (e.g., the scanner may have any number of independent transmit and receive channels) or may be obtained without the benefit of parallel MR. In the first instance, SAR variation within the patient is generally unknown. Accordingly, MR measurements 535, when obtained in vivo, may be acquired using power levels that are generally known to be safe in view of worst case conditions.

In act 540, electromagnetic field components are determined from MR measurements 535 to form one or more electromagnetic field maps. For example, any of the methods for determining one or more electromagnetic field components described above in act 440 of FIG. 4 may be used to characterize the electromagnetic environment. In one embodiment, all of the electromagnetic field components are determined (i.e., all E-field and B-Field components), however, fewer than all of the field components may be computed to generate electromagnetic field map 545.

In act 520, RFIM information 515 and electromagnetic field map 545 are used to compute one or more RFIM images. In particular, electromagnetic field map 545 may be used to constrain RFIM computations to condition and simplify the optimization. In instances where full electromagnetic field information is available, RFIM computations may be transformed into a linear problem that can be solved using standard matrix inversion techniques. Alternatively, the electromagnetic field information available in electromagnetic field map 545 may be used to constrain, for example, an iterative optimization scheme to reduce computation time and/or reduce the likelihood of the optimization converging to a local minimum. Electromagnetic field map 445 may be used in other ways to assist and/or facilitate RFIM computations used to generate RFIM image 527.

Accordingly, the result of method 500 is a dual image; an MRI image indicating the spatial variation of NMR signal strengths and an RFIM image indicating the spatial distribution of one or more dielectric properties (e.g., conductivity, permittivity, permeability, etc.). It should be appreciated that the RFIM image may include values for multiple dielectric properties. For example, RFIM computations performed in act 520 may generate the spatial variation of conductivity, permittivity and/or permeability. These values may be integrated together to form a single image or rendered into separate images. Moreover, the dielectric properties may be integrated with NMR values or may be viewed in separate images to, for example, facilitate detection and/or diagnosis of biological anomalies, such as cancer. By using MR measurements to improve RFIM, richer information of a variety of properties of the patient may be obtained.

Unlike other multi-modal imaging techniques (e.g., combining computed tomography (CT) and MRI), in embodiments using a scanner that employs the same RF coils for RFIM and MRI, RFIM information and MR measurements do not need to be registered or otherwise aligned. Because the information is obtained from the same equipment, relatively complicated and often error prone registration algorithms or time consuming manual registration may be eliminated. Moreover, the resulting images generated from the different modes may be overlayed, combined and/or viewed without having to register the images, making the use of the multi-modal images simpler, more straightforward and intuitive. Accordingly, in addition to using each of the technologies to improve the other, acquired images may be automatically registered due to the dual operation of the same equipment.

In some embodiments, act 520 may be repeated any number of times. For example, act 520 may be performed before and/or without assistance from MR measurements (e.g., electromagnetic field map 545) to estimate one or more dielectric properties, which can be used to determine electromagnetic field map 545 (e.g., via estimates of dielectric properties 525'). Act 520 may then be performed again using the electromagnetic field information computed in act 540. In this way, dielectric properties estimated in a generally unassisted RFIM computation may be used to bootstrap a subsequent refined RFIM operation. Other combinations of the acts illustrated in FIG. 5 may be used, as the aspects of the invention are not limited in this respect.

Figure 6:
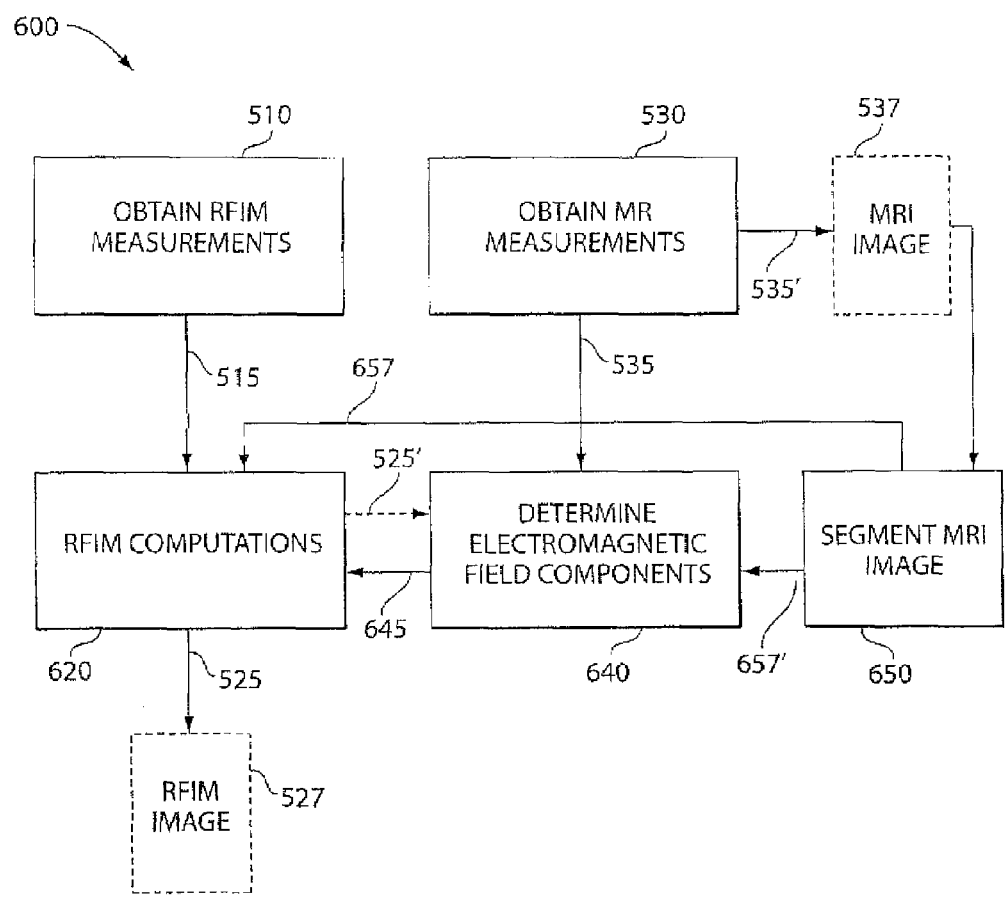
FIG. 6 illustrates a method of combining RFIM and MR information, in accordance with some embodiments of the present invention.

FIG. 6 illustrates a method for combining MR and RFIM information, in accordance with another embodiment of the present invention. Method 600 may be similar to method 500 described above. However, method 600 includes act 650, wherein MR image 537, reconstructed from MR measurements obtained in act 530, is segmented to identify generally homogenous regions within the image. For example, MR image 537 may be segmented into regions corresponding to organs and/or similar tissues (e.g., with respect to NMR signal strength). The segmented regions may then be used to constrain RFIM computations performed in act 620. In particular, segmented image 657 may be generated to provide prior information to assist in RFIM computations. It should be appreciated that segmented image 657 may be used alone or in combination with electromagnetic field map 545 to constrain and/or inform RFIM computations. In addition, segmented image 657' (e.g., some or all of the segmentation information in image 657) may be used to assist in electromagnetic field computations performed in act 640.

Figure 7:
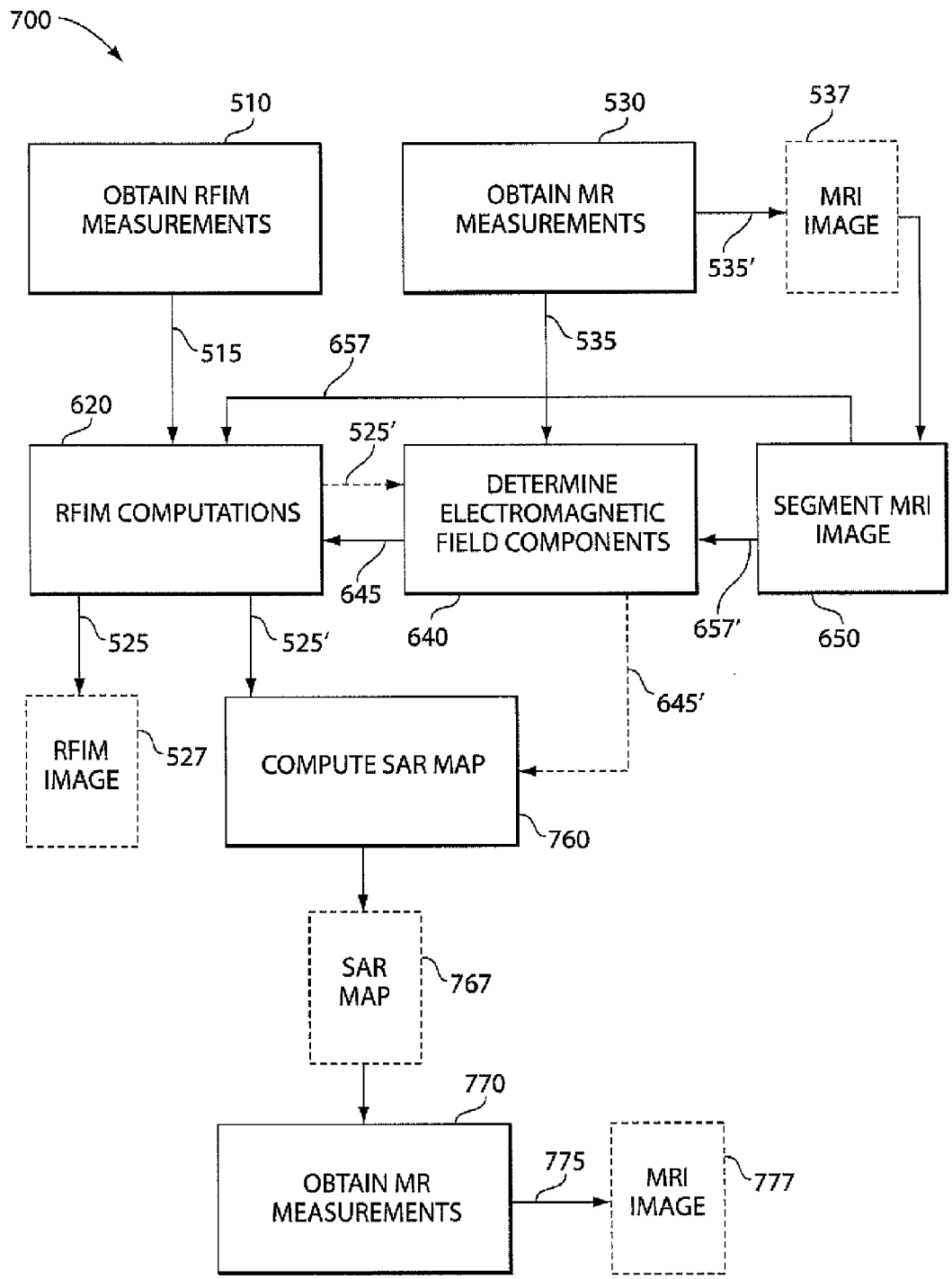
FIG. 7 illustrates a method of combining RFIM and MR to generate one or more SAR maps, in accordance with some embodiments of the present invention.

FIG. 7 illustrates a method for combining MR and RFIM information, in accordance with some embodiments of the present invention. Method 700 may be similar to method 600. However, in act 760, RFIM information 525' obtained during RFIM computation 620 may be used to generate one or more SAR maps 767. In particular, characterization of spatial variation of electrical properties allows for the determination of the SAR distribution at corresponding regions within the patient. As a result, RF power levels, guided by the SAR map, may be varied throughout the body to achieve optimal field strengths. That is, regions of relatively low SAR may be safely exposed to higher RF power, while regions of relatively high SAR (so-called "hot-spots") can be identified so that RF power deposition in those areas may be kept at lower levels. As discussed above, having one or more SAR maps to guide RF power deposition allows the benefits of high-field MR to be utilized in regions where corresponding RF power levels are known to be safe.

In act 770, MR measurements are again obtained, this time with the aid of SAR map 767. In particular, RF power can be varied in correspondence with the SAR maps to deliver the highest RF power deposition that remains below safety thresholds. Since SAR map 767 is available, the safety thresholds represent more precise levels determined from empirical measurements, rather than thresholds set to protect against worse case conditions. Therefore, RF power may be increased and tailored to the subject being imaged with reduced or eliminated risk of harmful exposure. The MR measurements 775 obtained in act 770 may be used to reconstruct an MR image 777. Because the MR measurements were obtained with less stringent constraints on RF power, MR image 777 may be acquired more rapidly and/or at a higher resolution and quality as compared to MR image 537.

In an alternative embodiment, electromagnetic field map 645' computed in act 640 may be provided to assist in the creation of SAR map 767, either alone or in combination with dielectric property information 525'. It should be appreciated that the higher resolution/quality MR measurements obtained, at least in part, due to SAR map 767, may be employed to generate improved electromagnetic field maps, which in turn may be employed in RFIM computations to improve resulting electrical property maps. This procedure may be repeated to obtain iteratively refined and higher quality MR and RFIM images, as discussed in further detail below.

Figure 8:
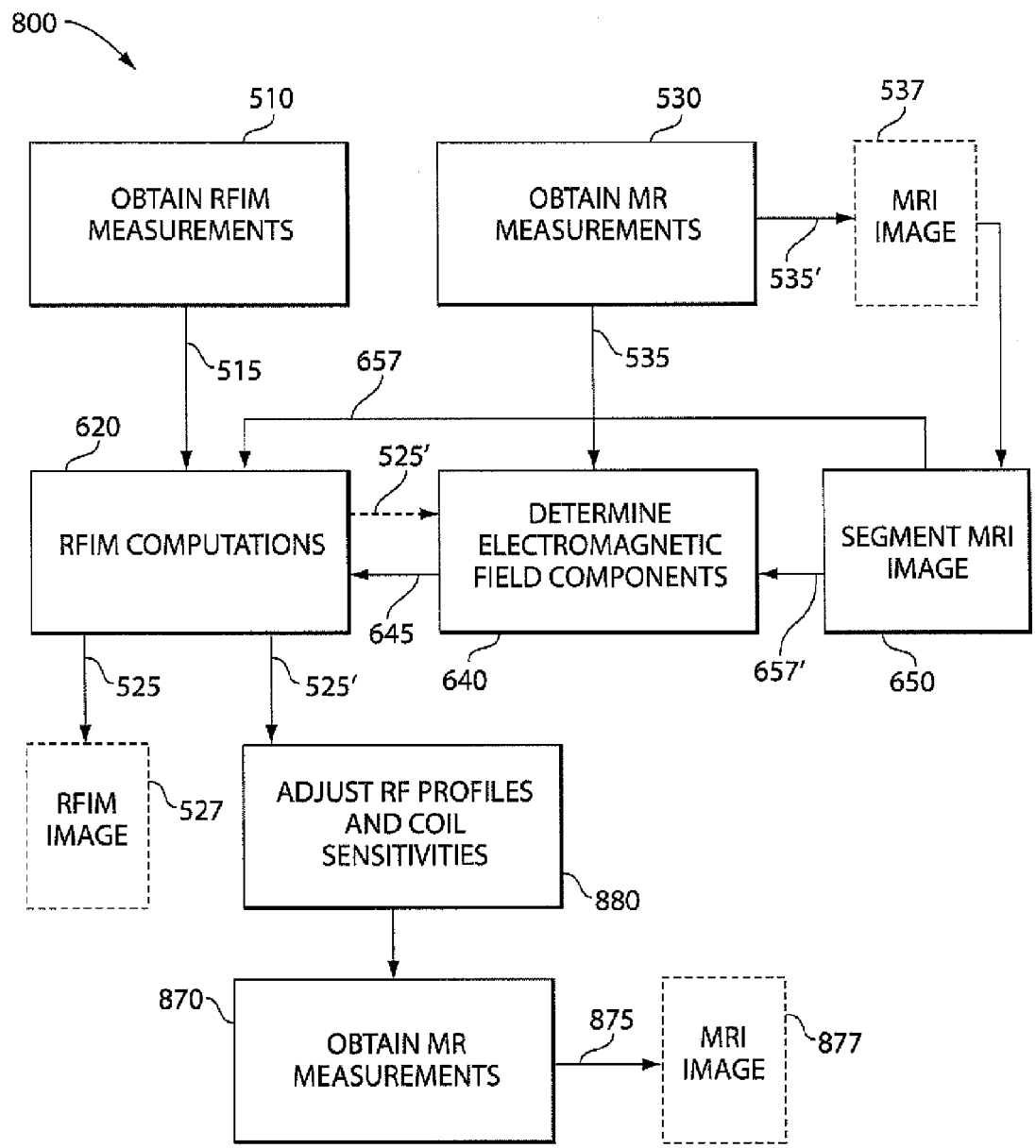
FIG. 8 illustrates a method of combining RFIM and MR information to adjust the parameters and/or operating characteristics of a scanner, in accordance with some embodiments of the present invention.

FIG. 8 illustrates another method of integrating MR and RFIM information, in accordance with some embodiments of the present invention. Method 800 may be similar to method 600 illustrated in FIG. 6. However, method 800 includes an act 880 to adjust RF transmit profiles and/or address coil sensitivity of the dual-mode scanner. For example, electromagnetic characteristics determined in acts 620 and 640 may be used to facilitate adjusting the RF transmit profiles. As discussed above, at high-field strengths, it becomes increasingly difficult to achieve homogenous RF pulse sequences over large volumes. Information on the electromagnetic environment in the presence of the subject being imaged, may be used to increase the homogeneity of the RF transmission sequences used to obtain MR measurements.

In addition, electrical properties determined from RFIM measurements may be used to adjust and/or calibrate the RF coils in the array. As discussed above, the load effects viewed as information in RFIM operations are seen as noise from an MR perspective. Accordingly, once the load effects have been characterized, this information may be used to tune the coils to compensate for this effect. Accordingly, the RF coils may be optimized for MR by reducing or eliminating signal degradation due to resonant frequency shifts caused by coil loading.

In act 870, MR measurements are obtained using the tuned RF coils and/or adjusted RF transmission profiles. MR scans with optimized transmit and receive coils generally provide higher SNR and result in higher resolution and/or higher quality images. Accordingly, one or more MR images 877 may be reconstructed using MR measurements 775 obtained from the scanner optimized using RFIM information. It should be appreciated that acts 760 and 880 may be combined before performing a second MR scan. In particular, SAR maps may be used to improve RF homogeneity and facilitate high-field MR and the RF coils may be tuned using the determined electrical properties to provide substantially improved MR images.

MR data obtained with such a system may then be used to inform and constrain RFIM reconstructions, thereby improving the quality and robustness of RFIM image acquisition. The improved RFIM data, in turn, along with additional calibration data, may be used to further improve the MR data, and to address many of the challenges associated both with high-performance parallel imaging and with high-field MRI. The resulting image information from MRI and RFIM may be merged to yield rapid, comprehensive, volumetric images at high spatial resolution with multiple complementary contrast mechanisms. As discussed above, unlike some examples of multimodal fusion, which require careful co-registration of disparate image information, MRI and RFIM data may be, in a sense, automatically co-registered, since, in some embodiments, the MR and RFIM information would be derived from the same equipment (e.g., the same RF transmit/receive coils), and since information from one may already have been used to obtain the other.

Figure 9:
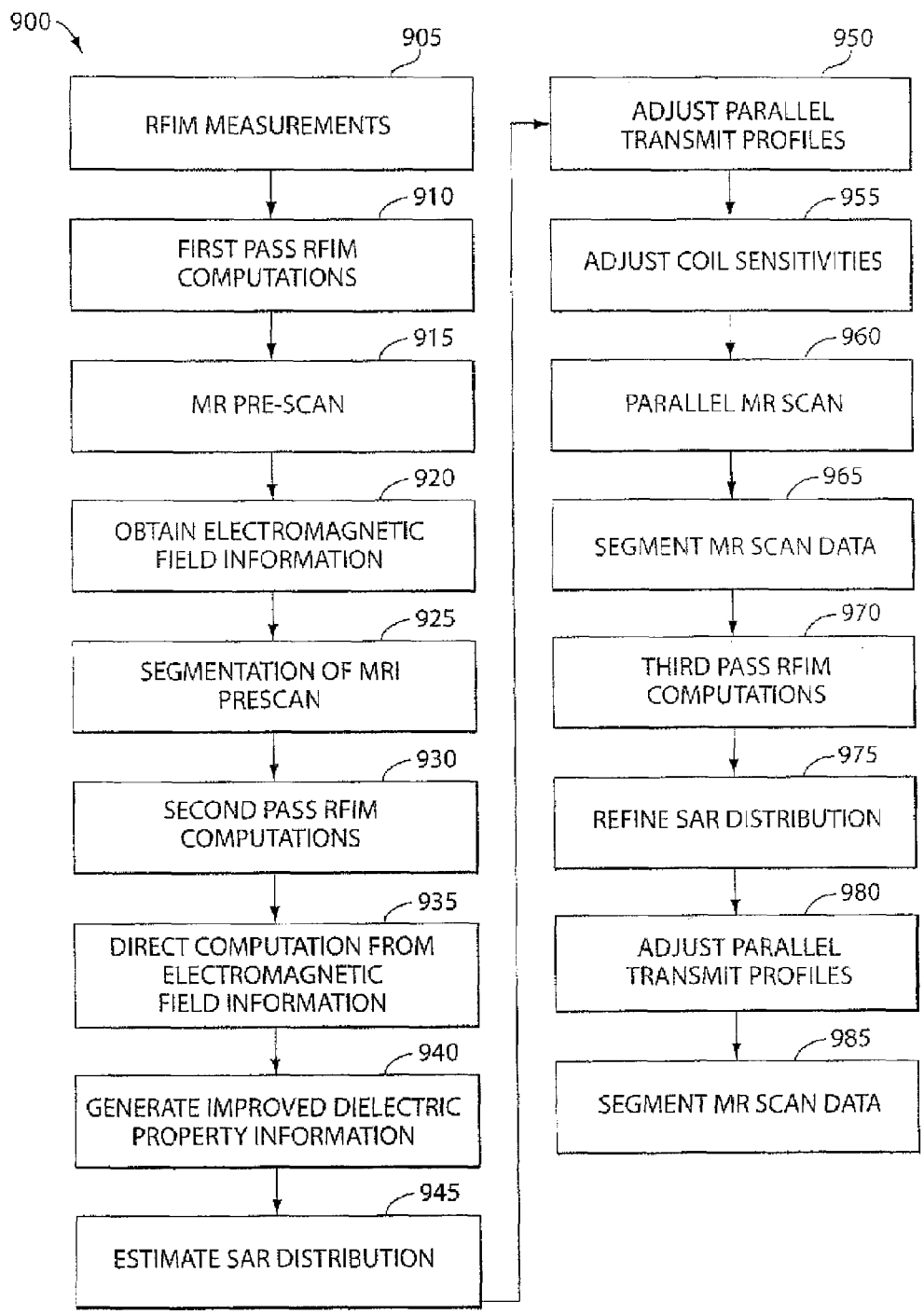
FIG. 9 illustrates a method of combining RFIM and MR information iteratively to improve data generated from one or both of RFIM and MRI imaging modalities, in accordance with some embodiments of the present invention.

FIG. 9 illustrates a method of using MR and RFIM information to iteratively improve one or both of the imaging modalities, in accordance with some embodiments of the present invention. The method illustrated in FIG. 9 may be particularly suited to in vivo imaging of the internal structure of some target portion of the human body in a scanner such as scanner 300 that is adapted to obtain MR and RFIM information using the same RF coil array. While method 900 is described in connection with a human body, it should be appreciated that the method may be used for other imaging procedures and applications as well, as the method is not limited for use with any particular type of object or subject to be imaged, or any particular implementation of a dual-mode scanner.

In method 900, RFIM measurements are obtained from a subject prior to, during, and following the placement of the body proximate an RF coil array of the scanner (act 905). The RFIM measurements are then used to perform a first pass RFIM computation to determine estimates of dielectric property variation within the body (act 910). The estimates may then be used to assist in determining electromagnetic field components, which in turn, may facilitate further refinement of RFIM computations. Next, an MR pre-scan may be performed to obtain MR measurements of the body (act 915). The MR pre-scan may be performed with relatively low spatial resolution (e.g., using conventional clinical power levels) and may be optimized for mapping electromagnetic fields through the body. The desired electromagnetic field components and/or dielectric property estimates may then be extracted from the MRI pre-scan data (act 920). The MR pre-scan data may also be segmented into organ and/or tissue classes (act 925) to further improve second pass RFIM computations.

A second pass RFIM computation may be performed using the electromagnetic field information obtained from the first pass RFIM and MR measurements to refine the mapping of dielectric property distribution in the body (act 930). Dielectric properties may also be computed directly from the electromagnetic field information obtained from the MR pre-scan (act 935). The dielectric property maps obtained from the second pass RFIM and direct computations may be compared, combined and/or integrated to obtain an improved dielectric property map of the body (act 940).

The electromagnetic field information and dielectric property information may then be used to estimate SAR distribution in the body (act 945). Based on the current best estimate of dielectric property variation (e.g., as obtained via acts 930-940), adjustment of parallel transmit profiles may be made to improve RF homogeneity and SAR distribution for subsequent MR scans (act 950). Parallel MR coil sensitivities may be adjusted based on known electromagnetic field profiles to obtain increased MR accuracy, SNR and resolution (act 955).

A second MR scan may then be performed using the optimized and/or tuned parallel RF coils (act 960). By utilizing the tuned coil array and generated SAR maps, the second pass MR scan may be performed at relatively high speeds and high field strengths, improving the resolution and/or quality of the resulting MR image. The image reconstructed from the second pass parallel MR scan may be a volumetric image of the target portion of the body. This volumetric image may be segmented to provide organ, tissue and/or suspect area (e.g., a biological anomaly) classification to improve subsequent RFIM computations (act 965). A third pass RFIM computation may then be performed using MR measurements (e.g., electromagnetic field information) and/or the segmented MR image to improve dielectric property mapping (act 970).

A second pass SAR computation may then be performed using the improved electromagnetic field and dielectric property information obtained from the second pass parallel MR scan and the third pass RFIM computation (act 975). The improved SAR estimates and dielectric property information may be used to refine the parallel transmit profiles in a second pass adjustment of the RF coil array (act 980). The second pass optimized scanner may then be operated to generate third pass parallel MR data to obtain a second volumetric parallel MR image of the internal structure of the targeted portion of the body (act 985). The second pass optimization and improved SAR distribution facilitates obtaining relatively rapid, high resolution MR images generated under generally high-field strength conditions that are safe for in vivo imaging of biological subjects, although the various operations are not limited to biological subjects.

It should be appreciated that the above process may be iterated any number of times to obtain increasingly refined RFIM and MR measurements. In addition, the above acts may be performed in any combination and in any sequence. Moreover, certain acts may be omitted or repeated more frequently as desired, as the aspects of the invention are not limited for use with any particular combination of operations or sequence of procedures.

Various embodiments described above make use of a unified RF transmit and receive system to exploit one or more synergies between MRI and RFIM. As discussed above, the availability of MR data from such a system provides valuable anatomical constraints for RFIM computations, facilitating an otherwise relatively challenging image reconstruction. In addition, the volumetric dielectric property data obtained from RFIM, as well as the multiple-port transmission capability employed in some embodiments to obtain loading and field mapping measurements, may be used to correct artifacts and address important safety concerns commonly encountered in MRI at high magnetic field strengths, as well as improving the quality of parallel imaging approaches which have their own synergy with high-field MRI.

In another embodiment, various aspects of the present invention are employed in the context of molecular imaging. The availability of a new axis of electromagnetic contrast can be used to develop new imaging agents, exploiting the chemistry and biology of RF dielectric contrast. Moreover, the speed of highly parallel imaging may also facilitate the use of new classes of MR contrast agents, for example, liquid-state hyperpolarized agents, which may increase signal-to-noise ratio by several orders of magnitude. In particular, contrast agents whose signal enhancement persist only for a short time may now be employed due to the speed increase of parallel MR.

As should be appreciated from the foregoing, there are numerous aspects of the present invention described herein that can be used independently of one another or in any combination. In particular, any of the above described MR and RFIM operations may be employed in any of numerous combinations and procedures. It should also be appreciated that in some embodiments, all of the above-described operations can be used together in any sequence, or any combination or subset of the operations described above can be employed together in a particular implementation, as the aspects of the present invention are not limited in this respect. In addition, the various operations may be performed on any type of device or apparatus, and are not limited to any particular implementation.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code, as the aspects of the invention are not limited to any particular type of software.

The one or more processors configured to execute instructions forming a computer program may be part of a computer or computer system having multiple computers located proximate one another or distributed over a network. The processor may be, for example, a digital signal processor, or any of various general purpose processors. Similarly, the one or more computers may be specialized computers, embedded computers, or any of various general purpose computers (e.g., a personal computer), as the aspects of the invention is not limited for use with any particular number, type, location, or implementation of processor and/or computer.

In this respect, it should be appreciated that one embodiment of the invention is directed to a computer-readable medium or multiple computer-readable media (e.g., a computer memory, one or more floppy disks, compact disks, optical disks, magnetic tapes, etc.) encoded with one or more programs that, when executed, on one or more computers or other processors, perform methods that implement the various embodiments of the invention discussed above. The computer-readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that, when executed, perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing, and the aspects of the present invention described herein are not limited in their application to the details and arrangements of components set forth in the foregoing description or illustrated in the drawings. The aspects of the invention are capable of other embodiments and of being practiced or of being carried out in various ways. Various aspects of the present invention may be implemented in connection with any type MR and/or RFIM imaging equipment of any configuration. No limitations are placed on scanner implementation. Accordingly, the foregoing description and drawings are by way of example only.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. An apparatus for obtaining magnetic resonance (MR) and radio frequency impedance mapping (RFIM) data, the apparatus comprising:
    a plurality of radio frequency (RF) coils capable of generating RF signals;
    an input controller capable of providing power to the plurality of RF coils to facilitate generating the RF signals, the input controller configured to power at least some of the plurality of RF coils to provide first RF signals and to power at least some of the plurality of coils to provide second RF signals adapted to obtain RFIM data;
    an output controller capable of obtaining measurements from the plurality of RF coils, the output controller configured to measure at least some of the RF coils to detect nuclear magnetic resonance (NMR) signals emitted from a region in response to the first RF signals to form, at least in part, first magnetic resonance (MR) data, and to obtain at least one impedance measurement from the plurality of RF coils to form, at least in part, first RFIM data; and
    at least one computer coupled to the input controller and the output controller to receive data obtained from the plurality of RF coils, the at least one computer configured to compute a first RFIM map indicating the spatial distribution in the region of at least one dielectric property, the first RFIM map computed based, at least in part, on the first RFIM data and the first MR data;
    wherein the at least one computer is configured to compute an electromagnetic field map indicative of a spatial distribution over the region of at least one electromagnetic field component based, at least in part, on the first MR data, and wherein computing the first RFIM map includes computing the first RFIM map based, at least in part, on the electromagnetic field map;
    wherein the at least one computer is configured to use the electromagnetic field map to constrain reconstruction of the first RFIM map.

2. The apparatus of claim 1, wherein the electromagnetic field map includes the spatial distribution of at least a magnetic field component.

3. The apparatus of claim 2, wherein the electromagnetic field map includes the spatial distribution of at least an electric field component.

4. The apparatus of claim 1, wherein the first RFIM map indicates the spatial distribution in the region of at least electrical conductivity.

5. The apparatus of claim 1, wherein the first RFIM map indicates the spatial distribution in the region of at least electrical permittivity.

6. The apparatus of claim 1, wherein the first RFIM map indicates the spatial distribution in the region of at least magnetic permeability.

7. An apparatus for obtaining magnetic resonance (MR) and radio frequency impedance mapping (RFIM) data, the apparatus comprising:
    a plurality of radio frequency (RF) coils capable of generating RF signals;
    an input controller capable of providing power to the plurality of RF coils to facilitate generating the RF signals, the input controller configured to power at least some of the plurality of RF coils to provide first RF signals and to power at least some of the plurality of coils to provide second RF signals adapted to obtain RFIM data;
    an output controller capable of obtaining measurements from the plurality of RF coils, the output controller configured to measure at least some of the RF coils to detect nuclear magnetic resonance (NMR) signals emitted from a region in response to the first RF signals to form, at least in part, first magnetic resonance (MR) data, and to obtain at least one impedance measurement from the plurality of RF coils to form, at least in part, first RFIM data; and
    at least one computer coupled to the input controller and the output controller to receive data obtained from the plurality of RF coils, the at least one computer configured to compute a first RFIM map indicating the spatial distribution in the region of at least one dielectric property, the first RFIM map computed based, at least in part, on the first RFIM data and the first MR data;
    wherein the at least one computer is further configured to:
        reconstruct a first MR image based, at least in part, on the first MR data;
        segment the first MR image into a plurality of regions, each region comprising substantially homogeneous image values to form a first segmented MR image; and
        compute the first RFIM map based, at least in part, on the first segmented MR image.

8. An apparatus for obtaining magnetic resonance (MR) and radio frequency impedance mapping (RFIM) data, the apparatus comprising:
    a plurality of radio frequency (RF) coils capable of generating RF signals;
    an input controller capable of providing power to the plurality of RF coils to facilitate generating the RF signals, the input controller configured to power at least some of the plurality of RF coils to provide first RF signals and to power at least some of the plurality of coils to provide second RF signals adapted to obtain RFIM data;

an output controller capable of obtaining measurements from the plurality of RF coils, the output controller configured to measure at least some of the RF coils to detect nuclear magnetic resonance (NMR) signals emitted from a region in response to the first RF signals to form, at least in part, first magnetic resonance (MR) data, and to obtain at least one impedance measurement from the plurality of RF coils to form, at least in part, first RFIM data, and at least one computer coupled to the input controller and the output controller to receive data obtained from the plurality of RF coils, the at least one computer configured to compute a first RFIM map indicating the spatial distribution in the region of at least one dielectric property, the first RFIM map computed based, at least in part, on the first RFIM data and the first MR data;

wherein the at least one computer is further configured to compute a first specific absorption ratio (SAR) map indicating a spatial distribution of SAR values over the region, the first SAR map determined based, at least in part, on the first RFIM map.

9. The apparatus of claim 8, wherein the input controller is configured to operate at least some of the plurality of RF coils to provide third RF signals to the object to induce an NMR effect, wherein the input controller is configured to vary field strengths of the RF signals as a function of location in the region, the spatial variation of the field strengths determined, based at least in part, on the first SAR map.

10. The apparatus of claim 9, wherein the output controller is configured to measure at least some of the plurality of coils to detect nuclear magnetic resonance (NMR) signals emitted from the region as a result of the third RF signals to form, at least in part, second MR data.

11. The apparatus of claim 10, wherein the at least one computer is further configured to compute a second RFIM map indicating a spatial distribution in the region of at least one dielectric property, the second RFIM map computed based, at least in part, on the first RFIM data and the second MR data.

12. An apparatus for obtaining magnetic resonance (MR) and radio frequency impedance mapping (RFIM) data, the apparatus comprising:
a plurality of radio frequency (RF) coils capable of generating RF signals;
an input controller capable of providing power to the plurality of RF coils to facilitate generating the RF signals, the input controller configured to power at least some of the plurality of RF coils to provide first RF signals adapted to obtain the RFIM data, and to power at least some of the plurality of coils to provide second RF signals adapted to induce an NMR effect in a region;
an output controller capable of obtaining measurements from the plurality of RF coils, the output controller configured to measure at least some of the RF coils to obtain at least one impedance measurement from the plurality of RF coils in response to the first RF signals to form, at least in part, first RFIM data, and to detect nuclear magnetic resonance (NMR) signals emitted from the region in response to the second RF signals to form, at least in part, first magnetic resonance (MR) data; and
at least one computer coupled to the input controller and the output controller to receive data obtained from the plurality of RF coils, the at least one computer configured to compute a first RFIM map indicating a spatial distribution in the region of at least one dielectric property based, at least in part, on the first RFIM data, and to compute a first specific absorption ratio (SAR) map indicating a spatial distribution of SAR values over the region, the SAR map determined based, at least in part, on the first RFIM map, wherein the input controller is configured to vary the field strengths of the second RF signals based, at least in part, on the first SAR map.

13. The apparatus of claim 12, wherein the at least one computer is configured to compute a second RFIM map indicating a spatial distribution in the region of at least one dielectric property, the second RFIM map computed based, at least in part, on the first RFIM data and the first MR data.

14. The apparatus of claim 13, wherein the at least one computer is configured to:
reconstruct a first MR image based, at least on part, the first MR data;
segment the first MR image into a plurality of regions, each region comprising substantially homogeneous image values to form a first segmented MR image; and
compute the second RFIM map based, at least in part, on the first segmented MR image.

15. The apparatus of claim 13, wherein the at least one computer is configured to compute an electromagnetic field map indicative of a spatial distribution over the region of at least one electromagnetic field component based, at least in part, on the first MR data, and wherein the at least one computer computes the second RFIM map based, at least in part, on the electromagnetic field map.

16. The apparatus of claim 15, wherein the at least one computer uses the electromagnetic field map to constrain reconstruction of the second RFIM map.

17. The apparatus of claim 16, wherein the electromagnetic field map includes the spatial distribution of at least a magnetic field component.

18. The apparatus of claim 17, wherein the electromagnetic field map includes the spatial distribution of at least an electric field component.

19. The apparatus of claim 16, wherein the at least one computer is configured to form a second SAR map indicating a spatial distribution of SAR values over the region, the SAR map determined based, at least in part, on the second RFIM map.

20. The apparatus of claim 19, wherein the input controller is configured to power at least some of the plurality of RF coils to generate third RF signals from the plurality of to induce an NMR effect in the region, the input controller varying the field strengths of the third RF signals as function of location in the region based, at least in part, on the second SAR map.

21. The apparatus of claim 20, wherein the output controller is adapted to measure at least some of the coils to detect nuclear magnetic resonance (NMR) signals emitted from the region as a result of the third RF signals to form, at least in part, second MR data.

22. The apparatus of claim 12, wherein the first RFIM map indicates the spatial distribution in the region of at least electrical conductivity.

23. The apparatus of claim 22, wherein the first RFIM map indicates the spatial distribution in the region of at least electrical permittivity.

24. The apparatus of claim 23, wherein the first RFIM map indicates the spatial distribution in the region of at least magnetic permeability.

25. The apparatus of claim 12, wherein the computer is configured to adjust transmit profiles for RF signals to be provided to the region, wherein the input controller is adapted to operate at least some of the plurality of RF coils to provide the second RF signals having the adjusted transmit profiles to induce an NMR effect in the region, and wherein the output controller is adapted to measure at least some of the plurality of RF coils to detect NMR signals emitted from the region as a result of the second RF signals to form, at least in part, the first MR data.

* * * * *